US005723293A

United States Patent [19]

Huang

[11] Patent Number: 5,723,293

[45] Date of Patent: Mar. 3, 1998

[54] DIAGNOSTIC METHOD AND KIT FOR DETERMINING RH BLOOD GROUP GENOTYPE

[75] Inventor: Cheng-Han Huang, New York, N.Y.

[73] Assignee: The New York Blood Center, Inc., New York, N.Y.

[21] Appl. No.: 553,888

[22] Filed: Nov. 6, 1995

[51] Int. Cl.$^6$ .................. C12Q 1/68; G01N 33/555; C07H 21/04; C12N 15/00

[52] U.S. Cl. .................. 435/6; 435/6; 435/91.2; 435/810; 436/501; 436/520; 436/68; 536/23.1; 536/23.5; 536/24.31; 536/24.33; 935/77; 935/78

[58] Field of Search .................. 435/6, 91.1, 91.2, 435/183, 270, 810; 536/23.1, 23.5, 24.31, 24.33; 935/5, 8, 9, 77, 78; 436/501, 520, 68

[56] References Cited

PUBLICATIONS

Luban NLC, "The new and the old—Molecular diagnostics and hemolytic disease of the newborn", *New England J Med* 329(9):658–60 (1993).

Agre P, and Cartron J–P, "Molecular biology of the Rh antigens", *Blood* 78:551–63 (1991).

Cartron J–P, and Agre P, "Rh blood group antigens: protein and gene structure", *Semin Hematol* 30:193–208 (1993).

Anstee DJ, and Tanner MJ, "Biochemical aspects of the blood group Rh (rhesus)antigens", *Baillieres Clin Haematol* 6:402–22 (1993).

Race RR, and Sanger R, *Blood Groups in Man*, 6th ed., Blackwell, Oxford (1975) pp. 178–260.

Tippett PA, "A speculative model for the Rh blood groups", *Ann Hum Genet* 50:241–47 (1986).

Chérif–Zahar B, Bloy C, Le Van Kim C, Blanchard D, Bailly P, Hermand P, Salmon C, et al., "Molecular cloning and protein structure of a human blood group Rh polypeptide", *Proc Natl Acad Sci USA* 87:6243–47 (1990).

Avent ND, Ridgwell K, Tanner MJA, and Anstee DJ, "cDNA cloning of a 30 kDa erythrocyte membrane protein associated with Rh (Rhesus)–blood–group–antigen expression", *Biochem J* 271:821–25 (1990).

Le Van Kim C, Mouro I, Chérif–Zahar B, Raynal V, Cherrier C, Cartron J–P, and Colin Y, "Molecular cloning and primary structure of the human blood group RhD polypeptide", *Proc Natl Acad Sci USA* 89:10925–29 (1992).

Kajii E, Umenishi F, Iwamoto S, and Ikemoto S, "Isolation of a new cDNA clone encoding an Rh polypeptide associated with the Rh blood group system", *Hum Genet* 91:157–62 (1993).

Arce MA, Thompson ES, Wagner S, Coyne KE, Ferdman BA, and Lublin DM, "Molecular cloning of RhD cDNA derived from a gene present in RhD–positive, but not RhD–negative individuals", *Blood* 82:651–55 (1993).

Colin Y, Chérif–Zahar B, Le Van Kim C, Raynal V, Van Huffel V, and Cartron J–P, "Genetic basis of the RhD–positive and RhD–negative blood group polymorphism as determined by Southern analysis", *Blood* 78:2747–52 (1991).

Mouro I, Colin Y, Chérif–Zahar B, Cartron J–P, and Le Van Kim C, "Molecular genetic basis of the human Rhesus blood group system", *Nature Genet* 5:62–65 (1993).

Walker RH et al., eds., *Technical Manual*, 11th ed., Chapter 11, pp. 229–258 American Association of Blood Banks, Arlington, Virginia (1993).

Zelinski T, "The use of DNA restriction fragment length polymorphisms in conjunction with blood group serology", *Transfusion*, 31:762–70 (1991).

Hopkinson DA, "The long [E/e] and the short [C/c] of the rhesus polymorphism", *Nature Genetics* 5:6–7 (1993).

Le Van Kim C, Chérif–Zahar B, Raynal V, Mouro I, Lopez M, Cartron J–P, and Colin Y, "Multiple Rh messenger RNA isoforms are produced by alternative splicing", *Blood* 80:1074–78 (1992).

Bennett PR, Le Van Kim C, Colin Y, Warwick RM, Chérif–Zahar B, Fisk NM, and Cartron J–P, "Prenatal determination of fetal RhD type of DNA amplification", *New England J Med* 329:607–10 (1993).

Fisk NM, Bennett P, Warwick RM, Letsky EA, Welch R, Vaugh JI, and Moore, G, "Clinical utility of fetal RhD typing in alloimmunized pregnancies by means of polymerase chain reaction on amniocytes or chorionic villi", *Am J Obstet Gynecol* 171:50–54 (1994).

Carritt B, Steers FJ, and Avent ND, "Prenatal determination of fetal RhD type" *Lancet* 344:205–06 (1994) (Letter).

Simsek S, Bleeker PM, and von dem Borne AE, "Prenatal determination of fetal RhD type", *New England J Med* 339:795–96 (1994).

Bennett P, Warwick R, and Cartron J–P, *New England J Med* 330(11):795–96 (1994) (Response to letter by Simsek et al.).

Huang C–H, Guizzo ML, McCreary J, Leigh EM, and Blumenfeld, OO, "Typing of MNSs blood group specific sequences in the human genome and characterization of a restriction fragment tightly linked to S–s–alleles", *Blood* 77:381–86 (1991).

Goossens, M, and Kan YY, "DNA analysis in the diagnosis of hemoglobin disorders", *Methods Enzymol* 76:805–17 (1981).

(List continued on next page.)

*Primary Examiner*—Bradley L. Sisson
*Attorney, Agent, or Firm*—Hoffmann & Baron, LLP.

[57] ABSTRACT

The invention provides a diagnostic method of determining Rh genotypes by the identification of the molecular basis of Rh polymorphisms. Specifically, the invention provides a method for directly determining Dd and associated CcEe genotypes with great accuracy, overcoming problems associated with traditional serologic typing methods and leading to a direct discrimination of D/D, D/d, and d/d genetic status. The diagnostic method allows genotyping of fetuses to assess the risk of hemolytic diseases caused by Rh alloimmunization and genetic counseling and/or testing of couples to predict the outcome of pregnancies in relation to Rh incompatibilities. The method of the invention preferably employs amplification of Rh nucleic acid sequences, and employs differential cleavage of RhD-, RhCc- and/or RhEe-specific nucleic acid sequences by a restriction enzyme. Furthermore, diagnostic kits for the determination of Rh genotypes are provided.

39 Claims, 9 Drawing Sheets

OTHER PUBLICATIONS

Huang C-H, Reid ME, and Blumenfeld OO, "Allelic exclusion of the Rh polypeptide genes revealed by analysis of transcripts expressed in the D-negative erythroid cells", (1995).

Huang C-H, Reid ME, and Chen Y, "Identification of a partial internal deletion in the RH locus causing the erythrocyte D—phenotype", *Blood* 86(2): (1995) (In press).

Huang C-H, and Blumenfeld OO, "Characterization of a genomic hybrid specifying the human erythrocyte antigen Dantu: Dantu gene is duplicated and linked to a delta glycophorin gene deletion", *Proc Natl Acad Sci USA* 85:9640–44 (1988).

Feinberg AP, and Vogelstein B, "A technique for radiolabeling DNA restriction endonuclease fragments to high specific activity" *Anal Biochem* 137:266–67 (1984).

Chérif-Zahar B, Le Van Kim C, Rouillac C, Raynal V, Cartron J-P, and Colin Y, "Organization of the gene (RHCE) encoding the human blood group RhCcEe antigens and characterization of the promoter region", *Genomics* 19:68–74 (1994).

Issitt PD, "The Rh blood group system, 1988: Eight new antigens in nine years and some observations on the biochemistry and genetics of the system", *Transfusion Med Rev* 3:1–12 (1989).

Socha WW, and Ruffie J, *Blood Groups of Primates: Theory, Practice and Evolutionary Meaning*, pp. 75–90, Alan Liss, New York (1983).

Salvignol I, Blancher A, Calvas P, Socha WW, Colin Y, Cartron J-P, and Ruffie J, "Relationship between chimpanzee Rh-like genes and the R-C-E-F blood group system", *J Med Primatol* 22:19–28 (1993).

Marsh WL, Chaganti RS, Gardner FH, Mayer K, Nowell PC, and German J, "Mapping human autosomes: evidence supporting assignment of rhesus to the short arm of chromosome No. 1", *Science* 183:966–68 (1974).

Chérif-Zahar B, Mattei MG, Le Van Kim C, Bailly P, Cartron J-P, and Colin Y, "Localization of the human Rh blood group gene structure to chromosome region 1p34.3–1p36.1 by in situ hybridization", *Hum Genet* 86:398–400 (1991).

MacGeoch C, Mitchell CJ, Carritt B, Avent ND, Ridgwell K, Tanner MJ, and Spurr NK, "Assignment of the chromosomal locus of the human 30–kDal Rh (rhesus) blood group–antigen–related protein (Rh30A) to chromosome region 1p36.13—p34" *Cytogenet Cell Genet* 59:261–63 (1992).

Kappes D, and Strominger JL, "Human class II major histocompatibility complex genes and proteins", *Ann Rev Biochem* 57:991–1028 (1988).

Huang C-H, and Blumenfeld OO, "MNSs blood groups and major glycophorins: Molecular basis for allelic variation", in Cartron J-P, and Rouger P, (eds.), *Blood Cell Biochemistry* 6:153–88, Plenum Press, New York (1995).

Hyland CA, Wolter LC, and Saul A, "Three unrelated Rh D gene polymorphisms identified among blood donors with Rhesus CCee (r'r') phenotypes", *Blood* 84:321–24 (1994).

DIAGNOSTIC METHOD AND KIT FOR DETERMINING RH BLOOD GROUP GENOTYPE

BACKGROUND OF THE INVENTION

This invention relates to a method for determining Rh blood group genotypes. More particularly, the invention relates to a molecular genetic method for the direct determination of Rh zygosities related to D/D, D/d, and d/d status and the associated CcEe genotypes.

The human red cell Rh (Rhesus) antigens form a complex blood group system of major importance in clinical medicine (Ref. 1). Of the Rh antigens, the D antigen is the most immunogenic and best known to stimulate alloimmunization. Individuals are phenotypically divided into RhD-positive and RhD-negative (also referred to as d) subgroups, based on the presence or absence of the D antigen on their erythrocyte membranes. Rh D/d incompatibilities and maternal alloimmunization to the D antigen are the most common and severe cause of hemolytic disease of the newborn (Ref. 2). Severely affected (anemic) fetuses may even need blood transfusion in utero, a dangerous invasive treatment. Other common and clinically important Rh antigens include the C, c, E and e (together also designated "non-D") antigens. Although they are not considered in the classification of Rh positive or negative status, the C, c, E, and e antigens have become relatively more common causes of fetal/neonatal hemolytic disease encountered in the United States. This is because immigrant families with prior Rh sensitization make up a sizable percentage of current Rh cases.

All of these Rh antigens or specificities reside in a family of nonglycosylated but palmitylated transmembrane proteins referred to as RhD, C/c and E/e polypeptides (Refs. 3–5). Two related structural genes, D and CcEe, encode the red cell membrane proteins carrying these antigens. While C/c and E/e are considered antigenic products of allelic genes, the D antigen has no serologically detectable antithetical "d" antigen (Ref. 6). In most cases, the D-negative phenotype has been associated with a complete absence of the D gene. In rare cases, the d phenotype may result from a partially deleted D gene or a silent D gene defective in expression.

Genetically, both the D and non-D antigens are expressed in autosomal codominant fashion and they are inherited en bloc through eight different Rh haplotypes, i.e., DCe, DcE, Dce, DCE, dCe, dcE, dce and dCE (Ref. 6). The frequency of these organizational frameworks is not random, but varies considerably among different ethnic populations. (See Table 1, described in detail elsewhere herein).

The structural basis for Rh haplotypes was not immediately apparent after Fisher's classic synthesis of genetic evidence gathered from population studies (Ref. 6). Over the years, several conceptual models, variously evoking the composition of the RH locus to include from one to three structural genes, have been put forward to account for the inheritance of Rh antigens (Refs. 6–7). The isolation of two different forms of Rh cDNA (Refs. 8–12) provides information necessary for the analysis of these models at the molecular level. Southern blotting and transcript sequencing analyses have indicated the presence of two genes, D and CcEe (non-D), in Rh-positive subjects, but only one gene (CcEe) in Rh-negative subjects (Refs. 12–14). This finding constitutes strong evidence supporting the two-gene model of the Rh locus (Ref. 7). Nevertheless, no correlation of the genomic maps with the Rh haplotype frameworks has been possible because of an inability to separate the extremely homologous D and non-D genes (Refs. 12, 13).

Historically, the determination of Rh genotypes has been made indirectly, being confined principally to methods of detecting and identifying Rh antigen expression on erythrocyte membranes. These serological methods employ antibodies or other compounds which identify and interact with the Rh proteins or portions thereof. For example, various antibodies specific for particular Rh antigens have been identified. Agglutination methods for detecting Rh protein and other blood group antigens are described in U.S. Pat. Nos. 5,324,479, 5,302,512, 5,213,963, 4,560,647, 4,403,042, 4,358,436, and 4,148,607. Numerous publications describing such conventional agglutination-type tests are available, such as Walker RH et al., eds., Technical Manual, 11 th ed., American Association of Blood Banks, Arlington, Va. (1993), the entire disclosure of which is incorporated herein by reference (Ref. 15).

These conventional serological methods are limited in that they provide information about expressed protein profiles, but are not capable of defining Rh antigen molecular structure or the molecular genetic makeup of the subject. To infer the inheritance of Rh genes, these methods generally require the acquisition of blood samples from not only the subjects being examined but also from other family members. Moreover, in the case of phenotyping a fetus, obtaining a blood sample involves a potentially dangerous procedure in which the fetus is susceptible to hemorrhage and possibly death. In any case, all of these conventional methods are deficient as diagnostic tools, because none of these methods provides any means by which Rh genotype might be determined.

It has been suggested to use restriction fragment length polymorphisms (RFLPs) in conjunction with serology testing to improve the understanding of blood group genes and their inheritance (Ref. 16). This proposal is severely limited in that it requires studying DNA markers which are not blood group genes themselves, but which are closely linked with particular blood group genes. Generally such yet-to-be-identified flanking DNA markers do not show a complete linkage disequilibrium with the structural genes. Thus, they cannot be used to determine Rh genotypes with precision, but might be developed as molecular tools for linkage analyses.

The molecular bases of certain polymorphisms which occur in the Rh locus have been elucidated (See, e.g., Refs. 10, 17–18). Various techniques have been used in these investigations, including the polymerase chain reaction (PCR), molecular cloning procedures, RFLPs, etc. None of the reported studies, however, teaches or suggests any method by which both Dd and CcEe genotypes can be simultaneously determined, and Rh zygosities related to D/D, D/d, and d/d status directly determined. Indeed, many of these investigations have recognized that the Rh system exhibits extreme polymorphism at the antigenic level which, in turn, is associated with great heterogeneity at the mRNA level (Ref. 18). As a result, it is increasingly apparent that current understanding of the Rh system is fundamentally incomplete.

Previous knowledge has simply not been sufficient to enable an accurate and reliable method of determining Rh genotypes. For example, previous studies have led to a method for the determination of RhD genotype by means of DNA amplification (Refs. 19–20). This method employs the PCR technique and a set of unique primers to amplify exon 10 of the RhD gene. The primer set, however, limits this method to a determination of D/D or d/d genotype, and is not capable of distinguishing the D/d and the associated CcEe genotypes. Moreover, this method has been found to be unreliable in certain situations, because only a small portion of the Rh genes, namely exon 10, is assessed by genomic amplification. Specifically, the use of the method in certain subjects results in anomalous DNA amplification fragments, causing either false negative or false positive results (Refs. 21–23). This method is, therefore, neither complete with respect to the major Rh antigens, nor is it sufficiently accurate to permit its routine use for patient counseling and management.

As a result, there exists a need for a method of safely, conveniently, and accurately detecting Rh genotypes, including both D and non-D genotypes. It would also be especially desirable to provide a method for determining Rh genotypes in a fetus without a requirement for obtaining blood samples. A test based on DNA samples taken from amniotic cells would allow the clinician to avoid the risk of harm to the fetus and to more accurately predict the potential of anti-Rh-associated hemolytic disease of the newborn.

SUMMARY OF THE INVENTION

The present invention provides a diagnostic method for the direct determination of Rh blood group genotypes. More particularly, the present invention provides a method for the differential determination of RhDd and associated CcEe genotypes.

In one embodiment, the invention provides a diagnostic method for the determination of Rh genotype of a subject. The method involves selectively cleaving genomic DNA to provide Rh gene fragments in an amount sufficient to provide information characterizing an Rh genotype. Preferably, the diagnostic method of the invention includes selectively cleaving genomic DNA to provide fragments of Rh genes which characterize the eight common Rh haplotypes. More preferably, the method enables the provision of fragments of Rh genes in an amount sufficient to distinguish RhD from RhC/c and E/e genes. Still more preferably, the method of the invention provides fragments which specifically characterize or identify one or more aspects of Rh genotypes associated with the RhD and/or RhCcEe genes. The method of the invention also permits identification of an Rh genotype, or provides information which can be employed with other tests or assays to more fully characterize the genetic blueprint underlying the expression of Rh antigens.

Preferably, the method of the invention involves the analysis of Rh gene(s) by means of a restriction enzyme which selectively or differentially cleaves a DNA sample (preferably including genomic DNA) to produce fragments unique to the D gene and/or the CcEe genes. The restriction enzyme is preferably selected to digest a DNA sample to provide Rh gene fragments which characterize or differentiate the D/d genotype and/or the C/c and E/e genotypes. More preferably, the restriction enzyme digestion cleaves genomic or other DNA differentially based on polymorphisms in the intronic regions of the Rh structural genes. Most preferably, the restriction enzyme will produce Rh DNA fragments which specifically characterize or differentiate individual Rh genes and allow precise determination of their combinations, i.e., the Rh genotypes. A highly preferred restriction enzyme for use according to the invention is SphI. Informative combinations of SphI with other restriction enzymes may also be employed.

In another embodiment, the diagnostic method of the invention includes amplifying DNA from a subject to produce multiple copies of the DNA of interest, in this case Rh DNA. Preferably, such amplification is accomplished prior to the selective cleavage of the Rh DNA. Amplification is achieved by methods known in the art such as polymerase chain reaction or ligase chain reaction, or a combination thereof.

Typically, DNA amplification is performed by means of an oligonucleotide primer or set of primers which amplifies Rh DNA. The amplified Rh DNA is then treated, i.e., digested, with a restriction enzyme, to produce Rh DNA fragments in an amount sufficient to provide information concerning Rh genotype of the subject.

In the method of the invention, it is possible to use one or more oligonucleotide primers which amplify Rh DNA. It is preferred, however, to employ primer(s) which selectively hybridize with and amplify Rh DNA. More preferably, it is desired that the primer or primers specifically hybridize with and amplify Rh DNA without substantial contribution from non-Rh DNA.

The method of the invention can employ a set of primers which amplify different segments of Rh DNA. For example, the method of the invention can employ primers which differentially amplify RhD DNA and/or RhCcEe DNA. For example, the primer set may include a combination of primers, including at least one which either selectively or specifically amplifies RhD DNA, and at least one which either selectively or specifically amplifies RhCcEe DNA. In this way, information can be derived permitting the differential determination of the D/d and the associated CcEe genotypes.

The method of the invention typically further includes examining the Rh DNA fragments to derive information permitting discrimination of one or more aspects of Rh genotype. Such discrimination involves identifying particular fragments which are commonly, preferably consistently, representative of part or all of specific alleles or haplotypes. Numerous methods are known for deriving information sufficient to accomplish such differential discrimination. For example, the method of the invention may include separating Rh DNA fragments, such as on the basis of molecular weight, electrophoretic mobility, chromatographic mobility, etc. Because restriction enzymes cleave DNA into discrete fragments of particular sizes, a separation of the fragments will reveal a fragment pattern. Once separated, some or all of the fragments may be specifically or non-specifically identified according to known methods. For example, the Rh DNA fragments may be stained non-specifically, relying on the fragment pattern itself for a derivation of genotype information. Alternatively, one or more of the fragments may be identified by means of a hybridization probe composition including one or more oligonucleotide probes which hybridize with one or more fragments. Such hybridization may be induced to uniquely or selectively identify particular fragments. Identification of probe hybridization may be accomplished by means of probes to which have been attached detectable moieties.

The method permits derivation of information characterizing, preferably specifically characterizing or differentiating, various aspects of Rh genotypes. The method advantageously enables the artisan to obtain information characterizing RhDd genotype, RhCc genotype, RhEe genotype, RhCcEe genotype, RhDCcEe genotype, and combinations thereof.

The method of the invention can include determining Rh genotype as described above, together with the determination of genotype of the subject with respect to other, non-Rh genes. Alternatively, the method may include a determination of specific phenotype information about the subject. In an especially preferred embodiment, for example, Rh phenotype is advantageously determined to provide confirmatory or complementary evidence of Rh genotype determination. Such phenotype determination may be performed by serological testing.

In another embodiment, a diagnostic kit is provided for performing the Rh genotype determination method of the invention. In this embodiment, the diagnostic kit of the invention enables determining Rh blood group genotype(s) by detecting target nucleic acid sequences, such as sequences specific to the RhD and/or RhCcEe genes. The kit includes a restriction enzyme which can differentially cleave a DNA sample to generate Rh DNA fragments providing information concerning Rh genotype. The kit may include an amplification primer or primer set, i.e., oligonucleotides that may be used to bind to or cause elongation through sequences specific to D and/or CcEe DNA. Typically, the primer is provided in a first reagent container, and the restriction enzyme is provided in a second reagent container.

The diagnostic kit may further include other container means, such as a microtiter plate having a plurality of wells. In such cases, the kit can include microtiter plates to which have been attached oligonucleotide capture probes having nucleic acid sequences which are substantially complementary to the D and/or CcEe target sequences.

In addition, the kit may include additional components such as reagents, diluents, buffers, as well as control samples. The kits may also include detection means, such as nucleic acid stains or oligonucleotide probes. Kits may be constructed and sold in any configuration which enables performance of the specific embodiments of the method of the invention. Generally, for example, each of these is provided in a separate container. The kits may further include means for acquiring an erythroid tissue sample from a subject, means for extracting DNA from tissue samples, means for detecting Rh DNA, etc., without limitation.

In a further embodiment, the invention provides a diagnostic composition for determining Rh genotype of a subject. In this embodiment, the composition includes DNA fragments characterizing all or part of the Rh genotypes of the subject. The characteristic DNA fragments result from selective cleavage of a DNA sample derived from a subject.

Accordingly, as a result of the invention, there is now provided a safe and convenient diagnostic method for differentially determining Rh genotype of patients. In particular, RhDd and RhCcEe genotypes can be determined selectively or in conjunction with each other and with other genotype information. There is now provided a method for determining Rh genotypes in a fetus in utero which can be performed even without requiring the taking of a blood sample. A test based on determining Rh genotype(s), in particular Dd and/or CcEe genotypes, from DNA obtained from a tissue sample such as amniotic fluid or chorionic villus, now allows the clinician to reduce the degree of risk to the fetus being tested. Moreover, the new diagnostic method permits the accurate prediction of the potential of anti-Rh-associated hemolytic disease of the newborn.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein.

DETAILED DESCRIPTION OF THE INVENTION

Figure 1:
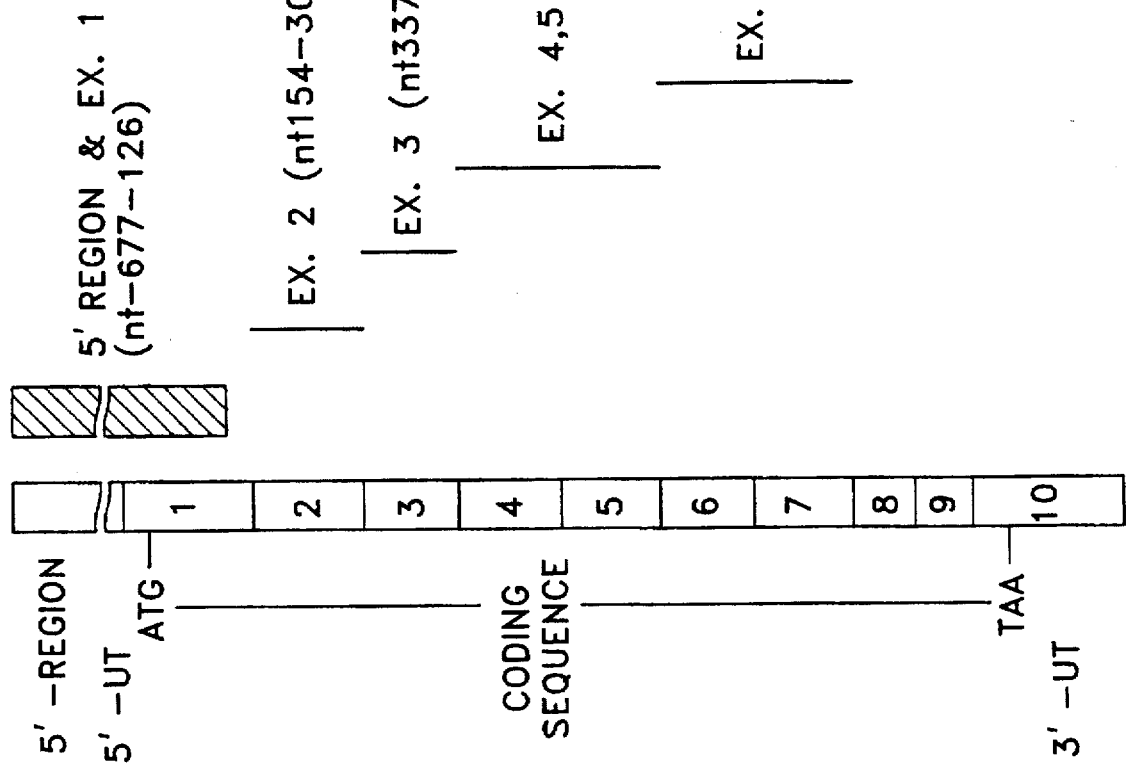
FIG. 1 is a diagram showing the relationships among a set of Rh gene probes used according to the method of the invention, which together span the 5' to 3' untranslated region of Rh cDNA.

As has been described in greater detail above, the determination Rh genotypes, especially with regard to Dd and CcEe genotypes, is of great clinical importance. However, until now the complexity of Rh genetics has been a significant burden which has never effectively been overcome. Despite such problems, it has now unexpectedly proven possible to characterize Rh genotypes with excellent precision and accuracy.

The invention provides a method for the differential determination of Rh genotypes based on a set of RFLPs which are located in, and are highly descriptive of, both of the major Rh structural genes, i.e., D and CcEe. Exon-specific cDNA and oligonucleotide probes have been used to map the major Rh genes and to determine the position of endonuclease cleavage sites. A panel of restriction endonucleases has been screened in an effort to identify a set of restriction fragments which would provide the information necessary for determining Rh genotypes. It was unexpectedly found that it was possible to use a single endonuclease to generate a set of restriction fragments which permits direct and specific characterization of RhDd and RhCcEe genotypes.

The segregation pattern of restriction fragment length polymorphisms in informative families was traced and their distribution among unrelated persons was examined. It was found that particular RFLP markers are co-transmitted with the various Rh haplotypes. This remarkable finding was unexpected, in view of previous efforts which have yet to completely define the molecular structure of the major Rh genes. The co-transmission of the new RFLP markers with the various Rh haplotypes not only allows correlation of genotypes with the corresponding blood group phenotypes, but also provides a direct approach to the determination of Rh zygosity related to the Rh-positive or negative status (DD, Dd or dd), as well as to Rh CcEe status (CCEE, CCEe, CcEE, CcEe, CCee, Ccee, ccEe, ccEE or ccee). These features clearly render the inventive method useful in determining Rh genotypes, and are expected to play a growing role in genetic counseling and prenatal assessment of Rh alloimmunization.

For purposes of more clearly and accurately describing the invention herein, certain terminological conventions have been adopted in the following discussion. These conventions are intended to provide a practical means for enhancing description of the invention, but are not intended to be limiting, and the skilled artisan will appreciate that other and additional interpretations may be implied.

In this description, for example, the term "D gene" is intended to refer to genes which encode Rh D proteins. The term "D protein" is intended to refer to protein which carries the D specificity or antigenic determinant. D/d genotype is said to be a product of the presence or absence (or silence) of a D gene in the genome, while the presence or absence of D protein expression determines D/d phenotype. It is noted that the term "d" or "d" is not generally understood to imply the existence of an allele, but refers to an absence of detectable D protein or D gene. Indeed, as has been noted elsewhere herein, no serologically detectable d antigen has been found, and no gene encoding a d protein has been identified.

By contrast, the term "CcEe gene" is intended to refer to genes which encode CcEe proteins. In turn, the term "CcEe protein" is intended to refer to protein which carries C/c and/or E/e antigenic specificities. Accordingly, the CcEe genotype of an individual is believed to be determined by the specific pair of CcEe alleles in his/her genome, while the individual's CcEe phenotype is believed to be determined by the expression of CcEe proteins and the combinations of expressed C/c and E/e determinants.

It should also be noted that the designations "D" and "CcEe" may be employed to identify proteins, peptides, antigens, nucleic acids, oligonucleotides, etc., which are traceable to or associated with the D and CcEe genes and proteins. In general, however, it is understood that Rh-related or Rh-based chromosomal DNA (including exons, introns, and parts thereof), nucleic acid templates, nucleic acid transcripts, as well as cDNA, may be designated by the use of italics, e.g., "*D*" and "*CcEe*". This usage is consistent with usage in the art.

"Polymorphic" or "DNA polymorphism" refers to the condition in which two or more variations of a specific DNA sequence coexist in the same interbreeding population. Polymorphic differences are caused by differences in amino acid sequence which may be due to events such as point mutations, gene rearrangements or alternative splicing. While a difference may exist between the nucleotide sequences of two versions of the same gene, such differences do not give rise to a phenotypic polymorphism unless a change in amino acid sequence is caused. Even so, if differences in nucleotide sequence can be detected even without a corresponding amino acid change, then genetic polymorphism still exists. In particular, if a change in nucleotide sequence causes the creation or deletion of a restriction enzyme cleavage site, then analytical use can be made of restriction fragment length polymorphisms. Typically, it is difficult to identify such RFLPs even in a single gene. Thus, it is quite unexpected that RFLPs have now been found which permit the determination of genotype with respect to two genes based on the use of a single restriction enzyme. The method of the invention takes advantage of restriction fragment polymorphisms to permit the determination of RhD and RhCcEe genotypes, either separately or in conjunction with one another.

As a result of the present invention, it is now possible to design probes and/or primers comprising nucleic acid oligomers or oligonucleotides which can be employed to detect polymorphisms in the Rh genes. The probes or primers suitable for this purpose preferentially hybridize with or are specific for particular restriction fragments or regions incorporating restriction sites of Rh genes. Preferably, the primer permits the amplification of DNA which includes a restriction polymorphism site. The amplified DNA can be differentially digested depending on the presence or absence of the restriction cleavage site, thereby enabling the determination of Rh genotype. Typically, but not necessarily, such a restriction polymorphism involves a site or region in which a point change in nucleotide sequence causes a change in the Rh gene product. Nonetheless, even if the restriction site change does not cause a phenotypic polymorphism, such a change is consistently associated with another mutation which does cause such a phenotypic polymorphism. Accordingly, the probes or primers include those which hybridize with higher frequency alleles as well as those which hybridize with lower frequency alleles.

Accordingly, a probe of the invention may be said to bind to or hybridize with Rh DNA if it recognizes a defined region of Rh DNA, such as a region which encodes a D or CcEe polymorphism locus. A primer of the invention may be said to amplify Rh DNA if it binds to or causes elongation through a defined region of Rh DNA. Thus, a primer amplifies *D* DNA or amplifies *CcEe* DNA if it preferentially amplifies all or part of the D locus or all or part of the CcEe locus, respectively. Moreover, the invention contemplates the use of "Rh primers" or primers which non-selectively amplify both *D* DNA and *CcEe* DNA. Such primers are possible due to the large measure of homology present in the D and CcEe genes. On the other hand, a primer is specific for a particular gene or allele, such as D ("D primer", if it specifically amplifies only DNA associated with the D gene, while a primer specific for CcEe ("CcEe primer"specifically amplifies only CcEe DNA.

It is generally preferred that probes or primers be capable of differentiating two alleles which differ by no more than a single nucleotide modification. It is known in the art that it is possible to control the specificity of hybridization by selectively constructing probes and primers and by adjusting hybridization or other experimental conditions. There may be situations, however, in which it would be desirable to employ probes which hybridize somewhat less selectively. Accordingly, it is within a particular context that a probe or primer according to the invention is said to be "substantially complementary" to a specific Rh sequence. That is, if the situation demands high precision, a probe or primer is substantially complementary to a target sequence if there exists only a very small probability that the oligomer will bind with a sequence other than the specific target sequence. In other situations, a probe or primer may be deemed to be substantially complementary to a target sequence if the probability of a unique hybridization is substantially less than 1.0. Thus, a probe or primer of the invention may be "substantially complementary" to a target region if it is either exactly complementary, or even only partially complementary, to the target region, depending on the required stringency of the method parameters.

Thus, the invention employs probes and primers which hybridize with fragments of either or both of the Rh genes. Such probes are useful when both of the Rh genes or transcripts thereof are desired to be characterized. Moreover, the invention provides probes and primers which include part or all of one or more introns in the Rh locus in chromosomal DNA. Such probes are useful when the Rh genes themselves are desired to be characterized and additional information is desired to be obtained about the structure of the gene in a particular individual. This is true of a highly preferred embodiment of the invention. For example, the use of the SphI enzyme requires the amplification of Rh intronic segments since no SphI cleavage sites are known in the Rh cDNAs.

The probes or primers of the invention may also include, as part of their nucleotide sequences, regions which are not substantially complementary to any region adjacent to or near a target sequence. Thus, in any probe or primer of the invention, at least a part of the probe or primer is substantially complementary to a target segment.

The nucleic acid oligomers of the invention may be used as probes or primers to identify the presence of target nucleic acid fragments, such as D and/or CcEe fragments, through binding to or hybridizing with such target sequences. Accordingly, the nucleic acid oligomers may be detectably labeled by being linked to a detectable marker moiety such as a fluorescent label, an electron dense substance, a reporter moiety, a specific or nonspecific binding moiety, or other detectable moiety such as is known in the art. Optionally, the oligomers of the invention may further include a reactive moiety permitting cross-linking with a target nucleic acid sequence. Furthermore, the oligomers of the invention may be linked to a substrate, for example, to a gel or resin to immobilize the oligomers.

The molecular genetic method of the invention generally involves obtaining DNA from a biological sample, preferably a sample of erythroid tissue, of a mammalian subject, typically a human patient. Commonly, the method is used to analyze a blood sample, but other types of samples which contain erythroid tissue are useful. In a particularly preferred embodiment, the invention provides a method for determining Rh blood group genotype in a fetus. In this embodiment, the preferred tissue sample includes a sample of amniotic fluid or chorionic villus. It is understood that such samples can also be obtained from sample libraries or tissue archives such as blood banks, or from forensic evidence, etc. Accordingly, the method may be used on a unique or irreplaceable sample or may be used to screen large numbers of samples.

The molecular genetic method described herein can easily be applied to DNA samples obtained from amniotic fetal cells and/or chorionic villus cells and is useful in determining the Dd and/or CcEe genotype of the fetus. This test can assist in the identification of those pregnancies at risk for hemolytic disease of the newborn resulting from Rh alloimmunization.

Once the tissue sample has been obtained, it is desired that the nucleic acid be extracted from the cells in the sample. This can be achieved by any method known in the art. See, for example, the method of Sambrook et al. (Ref. 24). The purified nucleic acid fraction is then employed directly for the Rh genotype determination, or may be stored until needed.

In the method of the invention, the nucleic acid sample is selectively amplified by means known in the art to generate an amplified nucleic acid product, in which a disproportionate fraction is Rh-related nucleic acid. "Amplification" according to the method of the invention refers to any molecular biology technique for detection of trace levels of a specific nucleic acid sequence by exponentially amplifying a template nucleic acid sequence. In particular, suitable amplification techniques include such techniques as the PCR and the ligase chain reaction (LCR). The PCR is known to be a highly sensitive technique, and is in wide use. The LCR is known to be highly specific, and is capable of detecting point mutations. In certain circumstances it is desirable to couple the two techniques to improve precision of detection. The PCR is a well-known technique and is described, for example, in Innis et al. (Ref. 25). The LCR is more recently developed and is described in Landegren et al. (Ref. 25) and Barany et al. (Ref. 27). An LCR kit is available from Stratagene. Other amplification techniques may be expected to be employed according to the method of the invention.

Regardless of the precise amplification technique employed for the method of the invention, one or more primers is employed. "Primer" as used herein refers to an oligonucleotide, whether natural, synthetic or semisynthetic, which is capable of initiating DNA synthesis for exponential amplification of a target or template nucleic acid sequence by an amplification technique. For PCR the primer acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. For LCR the primer is capable of annealing to a target nucleic acid and of being ligated to an adjacent primer to serve as a template for amplification. Also for purposes of the LCR, the primer generally includes paired sets of adjacent, complementary oligonucleotides which can anneal to single stranded target molecules and ligate together. For LCR amplification of DNA, the primers include two sets of adjacent, complementary oligonucleotides.

A primer is preferably an oligodeoxyribonucleotide and is single stranded for maximum efficiency in amplification, but may also be double stranded. If double stranded, the primer is generally first treated to separate its strands before being used to prepare extension products. Typically, LCR primers are double stranded. The exact length of a primer will depend on many factors, but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template.

"Primer," as used herein, may refer to more than one primer, particularly in the case where there is some ambiguity in the information regarding one or both ends of the target region to be amplified. For instance, if a nucleic acid sequence is inferred from a protein sequence, a "primer" is actually a collection of primer oligonucleotides containing sequences representing all possible codon variations based on the degeneracy of the genetic code. One of the primer oligonucleotides in this collection will be homologous with the end of the target sequence. Likewise, if a "conserved" region shows significant levels of polymorphism in a population, mixtures of primers can be prepared that will amplify adjacent sequences.

A primer or probe can be labeled, if desired, by incorporating a label detectable by spectroscopic, photochemical, biochemical, immunochemical, or chemical means. For example, useful labels include $^{32}$P, fluorescent dyes, electron-dense reagents, reporter molecules such as enzymes (as commonly used in ELISAs), biotin, or haptens or proteins for which antisera or monoclonal antibodies are available. Other labels may be used by the skilled artisan according to the invention. A label can also be used to "capture" the primer, so as to facilitate the immobilization of either the primer or amplified DNA on a solid support.

"Oligonucleotide" or "nucleic acid oligomer" refers to primers, probes, nucleic acid fragments to be detected, nucleic acid controls, and unlabeling blocking oligomers and is defined as a molecule comprised of two or more deoxyribonucleotides or ribonucleotides. The nucleic acid oligomers of the invention may be single-stranded oligomers of deoxyribonucleic acid (DNA) or ribonucleic acid (RNA). The exact size of an oligonucleotide will depend upon many factors and the ultimate function or use of the oligonucleotide. The oligodeoxyribonucleotides and oligoribonucleotides may be obtained or derived by known methods from natural sources. Alternatively, the oligonucleotides may be produced synthetically according to methods known in the art. Such methods include, for example, cloning and restriction of appropriate sequences and direct chemical synthesis by a method such as the phosphotriester method of Narang et al. (Ref. 28); the phosphodiester method of Brown et al. (Ref. 29); the diethylphosphoramidite method of Beaucage et al. (Ref. 30); and the solid support method in U.S. Pat. No. 4,458,066. It is preferred that the oligomers be at least substantially purified to avoid introduction of artifacts into the genotype determination method.

The method of the invention also involves the digestion of Rh nucleic acid by means of a restriction endonuclease, that is, an enzyme, usually of bacterial origin, which cuts or cleaves double stranded DNA only at defined sites. Because these enzymes exhibit such highly precise cleavage of DNA, a given restriction enzyme will produce a characteristic pattern of fragments any time it is employed to cleave the same region of DNA. In the event that a change in DNA causes a cleavage site or "restriction site" to be deleted or a new site to be created, the total amount of digestion and the distribution of "restriction fragments" may shift. Thus, the term "restriction fragment length polymorphism" or "RFLP" refers to the differences in DNA nucleotide sequences that are randomly distributed throughout the entire genome and that produce different restriction fragment patterns for different individuals upon digestion of genomic DNA with restriction endonucleases.

The restriction enzyme digestion process may be accomplished according to known methods. Preferably, the digestion process employs a single restriction enzyme. Combinations of such enzymes may be employed if they are effective in generating informative and/or practical restriction fragments. A particularly preferred restriction enzyme is SphI, which, as will be seen below, has shown itself to be well suited for performing the method of the invention.

The restriction enzyme digestion is analyzed according to the invention to derive or produce information concerning Rh genotypes. The type and extent of the desired information, will affect the choice of restriction enzyme. For example, if RhDd and RhCcEe genotype information is desired to be obtained, the SphI enzyme has been found to be unusually useful. Other enzymes might be chosen when such complete information is not required. The skilled artisan will appreciate that the method of the invention can be modified in other ways to suit the practical requirements of particular assays of Rh genotypes.

The effectiveness of a restriction enzyme or combination of such enzymes can be determined by employing means for the separation of the resultant restriction fragments. Various such means are known to provide useful results. A preferred method in the art is fragments separation by means of polyacrylamide gel electrophoresis (PAGE). This method was employed in the Examples described hereinbelow.

The restriction fragments can be identified by means of specific probes. Suitable assay techniques for purposes of the present invention are known in the art. For example, such detection can be accomplished using a dot blot format in which unlabeled amplified sample is bound to a membrane and the membrane is incubated with labeled probe(s) under suitable hybridization conditions. Unhybridized probe is removed by washing and the membrane is then examined for the presence of labeled probe. Another suitable approach is accomplished in tandem with PAGE in which the separated fragments are stained non-specifically with a nucleic acid-staining substance such as ethidium bromide. Such methods are described, for example, in Sambrook et al., *Molecular Cloning: A Laboratory Manual*, 2d. ed., Cold Spring Harbor Laboratory, New York (1989) (Ref. 24). Other suitable methods will suggest themselves to the skilled artisan.

The method of the invention may further include steps related to the determination of Rh genotypes through inferences based on Rh serological phenotypes. For example, to avoid misleading or false results, it may be desirable to supplement or confirm the information gained from genomic testing with conventional serological testing. In addition, certain restriction enzymes may be used according to the invention which produce somewhat ambiguous results inasmuch as the resultant set of restriction fragments might fail to uniquely describe every genotype. In such cases, it may be possible to generate unique information for each and every genotype by employing serological testing in conjunction with genomic analysis using a restriction enzyme. Such serological testing steps may be performed either prior to, in parallel with, or after the prescribed genomic testing. Moreover, the planning of testing procedures may be based on preliminary partial results which rule out or imply the possibility of, for example, certain rare genotypes. It may also be desirable to perform genotype testing for other markers or blood groups together with the Rh genotyping method of the invention. For example, the genotyping method described in U.S. Pat. No. 5,589,336, or application Ser. No. 08/484,570 filed Jun. 7, 1995, relating to the determination of Kell genotypes, may be performed in conjunction with the method of the invention to provide counsel as to a broader spectrum of possible difficulties in pregnancy.

The Rh genotype determination methods of the invention are of particular utility in the determination of the genotype of fetuses to avoid hemolytic disease of the newborn. The methods of the invention are also useful, however, in a variety of other situations in which molecular genetic information about a person is desired. For example, the methods of the invention are useful in situations in which it is desired to obtain information concerning the identity of an individual from forensic samples. Alternatively, the methods of the invention are useful for obtaining genetic information enabling the determination of paternity in those situations in which paternity is in doubt or dispute. In addition, the methods of the invention are useful for the determining the Rh genotype of a recipient of a blood transfusion, as well as for the screening of stored blood for Rh genotypes, to avoid transfusion incompatibility. Other applications of the methods of the invention will suggest themselves to the skilled artisan.

The following examples are intended to assist in a further understanding of the invention. The particular materials and conditions employed are intended to be further illustrative of the invention and are not limiting upon the reasonable scope thereof.

EXAMPLES

For each of the Examples described herein, the molecular biology techniques employed were performed generally in accordance with methods accepted in the art. See, for example, Sambrook et al. (Ref. 24), and Innis et al. (Ref. 25), the disclosures of which are incorporated herein by reference.

Human Subjects

As described in greater detail below, 86 human subjects were studied. Of these, 71 were normal, whereas 15 carried low incidence Rh antigenic variants or Rh deficiency syndromes. The group of normal subjects included 38 Caucasians, 16 Blacks, 12 Asians (Chinese, Japanese and Indian), three native Americans and two Black-Asians. Subjects were either randomly chosen or selected on the basis of known Rh phenotypes (such as the selection of Rh-negative individuals). In addition, the subjects were either unrelated individuals or related members of families.

The Rh antigenic specificities of blood samples (phenotypes) were determined by standard hemagglutination tests. Of normal subjects, 48 were determined to be Rh-positive, and 23 were Rh-negative. The D, C, c, E, and e blood group phenotypes are summarized as follows:

Rh-positive: 17 D+C+c+E-e+, 10 D+C-c+E-e+, 8 D+C+c-E-e+, 7 D+C+c+E+e+, 3 D+C+c-E+e, 2 D+C-c+E+e-, and 1 D+C-c+E+e+; and Rh-negative: 11 D-C-c+E-e+, 5 D-C-c+E+e+, 2 D-C-c+E+e-, 2 D-C+c+E-e+, 2 D-C+c-E-e+, and 1 D-C+ c+E+e+.

With regard to the Rh genetic variants, all 15 subjects were unrelated. Five of these showed absence of non-D antigens (3 D-, 1 DC$^w$-, and 1 Dc-), three exhibited Rh deficiency (2 Rhnull and 1 Rhmod), and the remainder carried low incidence antigens.

Preparation of Genomic DNAs

In the following Examples, high molecular weight genomic DNAs were isolated from human and nonhuman primate peripheral leukocytes by either a total cell lysis procedure (Ref. 31) or a sequential cell lysis method (Ref. 32).

Preparation of Genomic Probes

Nucleic acid probes used in the following analyses of Rh genes included cDNA, genomic DNA, and oligonucleotide probes. Rh cDNA clones encoding an Rh peptide have been isolated, as published by Chérif-Zahar et al. (Ref. 8) and Avent et al. Ref. 9). Representative cDNA nucleotide sequences are defined by SEQ ID NO:1, (Ref. 8) and SEQ ID NO:2 (Ref. 9), each encoding a corresponding amino acid sequence defined by SEQ ID NO:3.Rh cDNA probes encompassing the 5'0 region (exons 1 to 4) and the 3' region (exons 4 to 9) were synthesized by reverse transcriptase-polymerase chain reaction (RT-PCR). The RT-PCR was performed using primers selected from published sequences (Refs. 8–9), according to a previously described method (Ref. 33). Exon-specific probes were generated by PCR amplification, using a thermostable DNA polymerase (Ref. 34). The genomic probe containing the 5' region and a portion of exon 1 (designated Ex 1) was amplified from a purified Rh phage clone (Ref. 33). Probes directed to other exons, including exon 2 to exon 10, were selectively amplified from Rh cDNAs. All DNA probes were purified by native polyacrylamide gel electrophoresis (PAGE) according to conventional methods.

FIG. 1 shows the sizes and nucleotide positions of the exonic probes employed for these studies. The sequence of full-length Rh cDNA spanning the 5' to 3' untranslated (UT) region is divided into 10 exons, as drawn. The locations of initiation and termination codons are illustrated. The cDNA probes specific for individual exons are shown by vertical lines, and their nucleotide positions relative to the first residue of codon ATG are indicated. All of the probes used in these examples cross-hybridize with both D and non-D Rh polypeptide genes. Oligonucleotide probes (25 to 27 mers) were synthesized on a 380A automated DNA synthesizer and purified by 15% PAGE containing 7.0 mol/L urea. These oligomers were mainly used to confirm the results of exon mapping (see below).

Exon Mapping by Southern Blot and Direct Gel Hybridizations

Genomic DNAs were digested to completion with restriction endonucleases, electrophoresed on 0.8% agarose gel and subjected to either Southern blot (Ref. 35) or direct gel hybridization (Ref. 36) using labeled DNA probes. The DNA probes were labeled with $\alpha$-$^{32}$P-dCTP by the random primer extension method (Ref. 37). Synthetic oligomer probes were labeled with $\gamma$-$^{32}$P-ATP by forward reaction of the $T_4$ polynucleotide kinase (Ref. 24) Washing conditions were adjusted as necessary to assure specific hybridizations with the probes as described previously (Refs. 31, 36).

EXAMPLE 1

Identification of RFLPs Associated with the D and Non-D Genes

Using the Rh cDNAs as probes, genomic DNAs from unrelated individuals were analyzed in an effort to identify RFLPs that might be linked with the Rh genes. A panel of restriction endonucleases (BamHI, EcoRI, HindIII, PstI, and SphI) was tested according to conventional methods (Refs. 31, 33). The enzyme SphI was found to be uniquely informative, in that this was the only restriction endonuclease in the panel which permitted D and non-D gene fragments to be readily distinguished.

Figure 2:
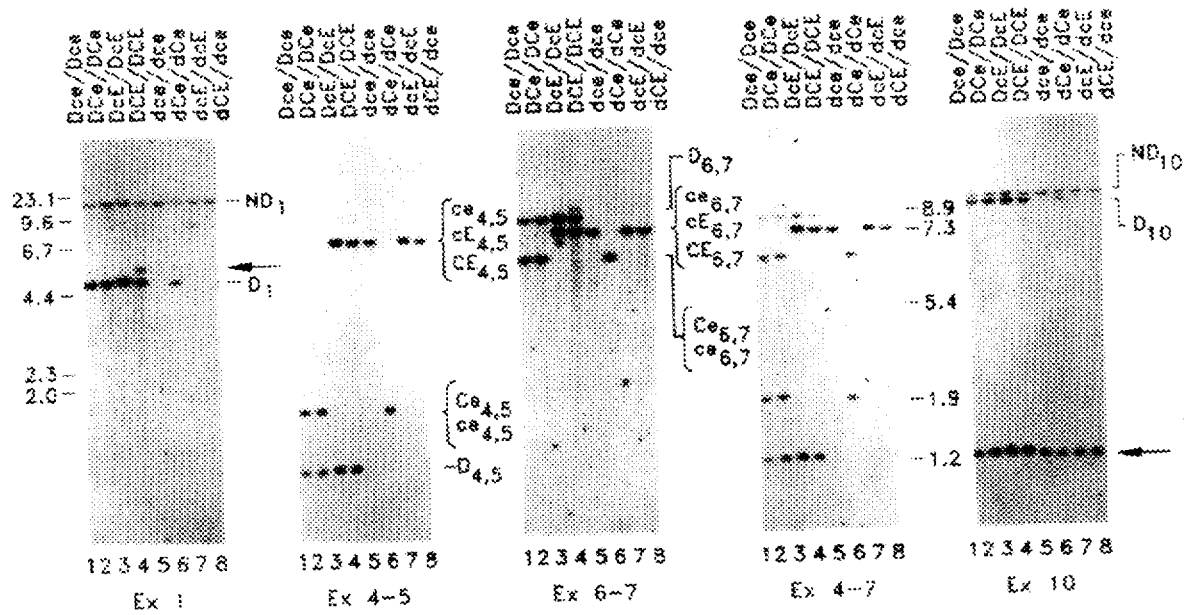
FIG. 2 shows a Southern blot of genomic DNAs from eight unrelated individuals prepared according to the method of the invention.

FIG. 2 shows the pattern of SphI RFLPs in eight unrelated individuals bearing the common haplotypes (4 Rh-positive and 4 Rh-negative). Genomic DNAs were digested with SphI, blotted onto filters, and hybridized with probes as indicated. Lanes 1 to 7 represent individuals who were informative homozygotes for given haplotypes. Lane 8 shows a dCE/dce heterozygote, as dCE/dCE homozygotes are very rare among human populations. It was also noted that the dCe/dCe homozygote carried a partial deletion in the D gene. The DNA size marker is indicated at the left margin of FIG. 2, and the origin of restriction fragments from D and non-D genes is at the right margin. Note that there are three separate exon 10-containing fragments; the band that is missing in Rh-negative (i.e., Rh d) is assigned as exon 10 of the D gene ($D_{10}$). Based on extensive analysis, four SphI RFLP frameworks in the genomic region encompassing exon 4 through exon 7 were recognized which correlated with the occurrence of distinct Rh haplotypes (Table 1).

Of the five bands detected by Ex4–7, the 8.9 and 1.2 kb bands were found only in individuals carrying the Rh-positive haplotypes. It was inferred that these fragments were most likely derived from the D gene. The 7.3, 5.4 and 1.9 kb fragments were observed in both Rh-positive and Rh-negative individuals, indicating that these fragments originate from the non-D gene(s).

Compared with the D-specific bands in Rh-positive haplotypes, the allelic fragments from ce, cE, Ce and CE varied in size. Moreover, the frequency of their occurrence was apparently related to the linkage status of D or d (Table 1). Specifically, the ce gene was found to produce either one or two bands when it occurred as Dce, but only one band in the dce haplotype. The cE and CE genes were associated with the presence of the 7.3 kb fragment regardless of their linkage with D or d. The fourth alternative, i.e., the Ce gene, always gave rise to two bands when cis to D. However, when d occurred cis to Ce, the Ce gene resulted in either one or two bands (Table 1). All other probes, including Ex 1 and Ex 10 (FIG. 2, panels 1 and 5), were less discriminatory due to the co-migration of non-D gene fragments.

EXAMPLE 2

A Comprehensive SphI Map for the D Gene and Non-D Alleles

Figure 3:
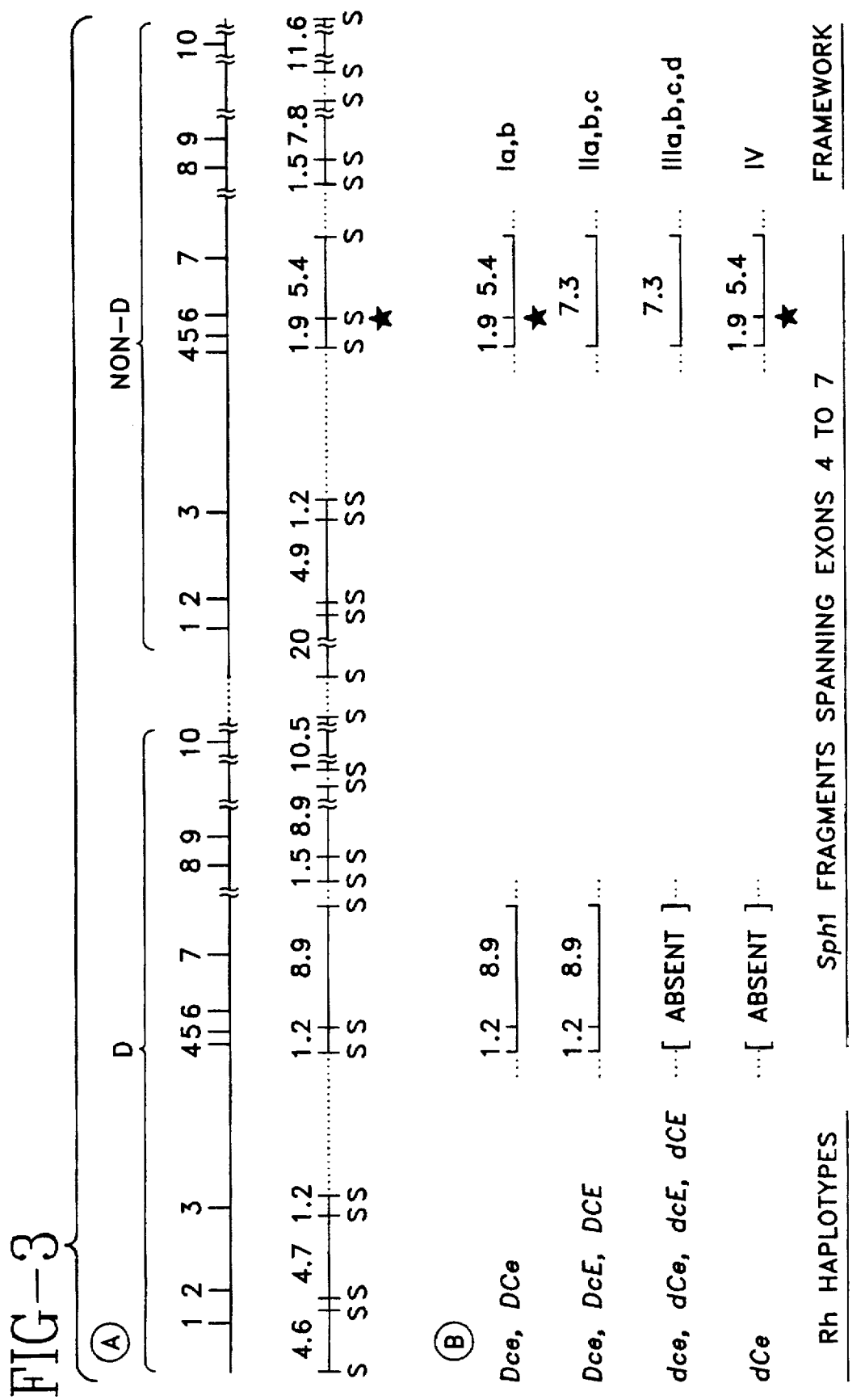
FIG. 3 is a comprehensive SphI restriction map for the Rh polypeptide genes, including schematic representation of the distribution of exons in the D and non-D genes as well as the relationship between the SphI RFLPs and Rh haplotypes.

A sequence search showed that there is no SphI cutting site in Rh cDNA. That is, SphI cuts Rh-related DNA only in intronic regions, if at all. Accordingly, it was inferred that each of the restriction fragments generated using SphI should contain at least one exon. Taking advantage of this feature, the exon content of various SphI bands was determined, and a comprehensive restriction map for the major Rh genes was derived, as shown in FIG. 3A. The locations and approximate distances (in kb) of SphI(S) cleavage sites that flank each exonic fragment are indicated. The assignment of exons was based on the parallel analysis of Rh-positive and negative individuals and on the fact that the D gene was completely absent from the dce, dcE and dCE haplotypes (FIG. 2). These results, obtained by use of exon-specific probes (FIG. 1), were further confirmed by direct gel mapping with synthetic oligonucleotides (data not shown).

FIG. 3A shows that the structural organization of D is quite similar to that of the non-D gene (Ref. 38). Nevertheless, the majority of D exons (8 out of 10 except exons 3 and 8) were distinguishable from those of the non-D gene because of the asymmetric distribution of SphI cleavage sites. Although some fragments originating from different regions of the two genes co-migrated, they could be readily differentiated on the basis of their exonic content.

It was apparent for all Rh genes that while their introns 4 and 6 lacked the SphI recognition sequence, introns 1, 2, 3, 7, 8 and 9 each retained at least one cutting site. In the case of intron 5, it harbored a unique SphI site in the D gene, but was polymorphic for the non-D alleles (FIG. 3A). This distribution of SphI cleavage sites permits a full explanation of the banding patterns observed among the eight Rh haplotypes (FIG. 2), and thus establishes the relationship between the SphI RFLP frameworks and Rh haplotypes (FIG. 3B).

EXAMPLE 3

Transmission of SphI RFLPs with Rh Haplotypes in Families

To explore whether the SphI RFLPs could be used to determine the Rh genotypes, their transmission was traced in several families. This tracing enabled the establishment of a correlation of the genotypes with the phenotypes (Table 2).

Figure 4:
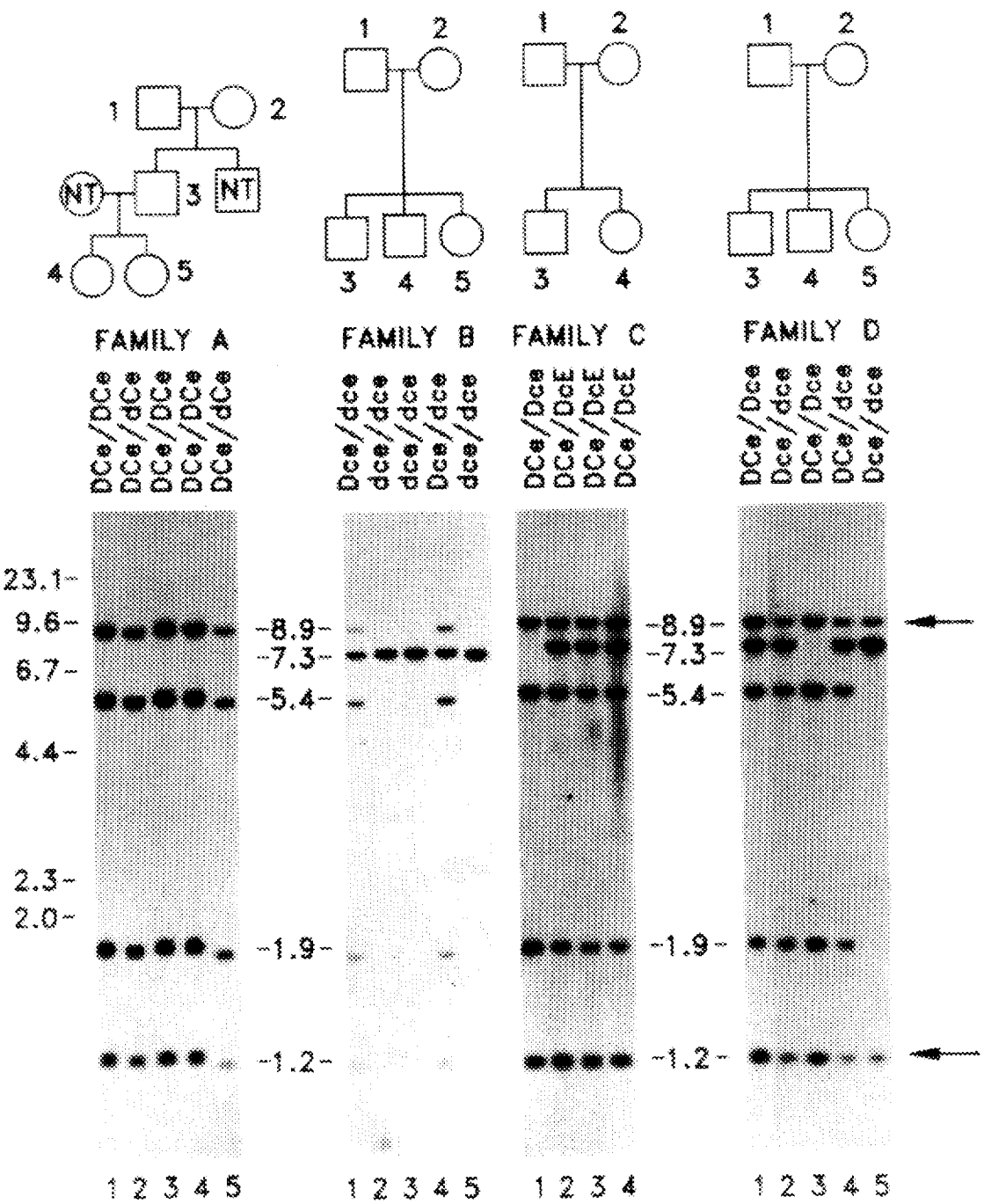
FIG. 4 shows a Southern blot of genomic DNAs from four families carrying different Rh haplotypes prepared according to the method of the invention, along with pedigrees of each family.

FIG. 4 shows a Southern blot of genomic DNAs of four families (A–D). Each individual in each family is assigned a number. Certain family members were not examined (designated NT in the family trees) due to unavailability of blood samples. The genomic DNAs were digested with SphI, and hybridized with Ex4–7. Gel lanes are matched with family pedigree, and the deduced genotypes are shown. The size of each SphI band is noted, and the D-specific bands are marked by two arrows at the right margin of panel 4.

In family A, all members were phenotypically D+C+c– E–e+. Such uniformity of phenotype among related individuals could result from two genotypes: DCe/DCe or DCe/dCe. Using the method of the invention, genomic blots indicated that family members A1, A3 and A4 were DCe/DCe homozygotes, whereas A2 and A5 were DCe/dCe heterozygotes (FIG. 4, panel 1). This conclusion was supported by a decreased intensity of D-specific bands in the latter two subjects.

In family B, the inference of two genotypes (Dce/dce and dce/dce) was more straightforward. As shown above, Dce and dce haplotypes are specified by different RFLP frameworks (Table 1). Accordingly, individuals with the Dce/dce genotype should display a SphI banding pattern different from those carrying the Dce/Dce or dce/dce genotype (FIG. 2). This was indeed the case for family B in which members B1 and B4 could be unequivocally defined as Dce/dce heterozygotes (FIG. 4, panel 2 and Table 2). These results illustrated a direct determination of Rh zygosity related to the Rh-positive or negative status (D/D, D/d or d/d).

The genotyping of family C was complicated by the expression of multiple Rh phenotypes which could be specified by three or six haplotype combinations (Table 2). Nevertheless, the finding of no decrease of intensity in the D gene bands (FIG. 4, panel 3) excluded the involvement of all d-containing haplotypes. Therefore, C1 should bear the DCe/Dce genotype, and the others should bear either the DCe/DcE or the DCE/Dce genotype. If C2 carried DCe/DcE (which would be the most probable case), both C3 and C4 should have inherited DCe from C1 and DcE from C2 (Table 2).

Figure 5:
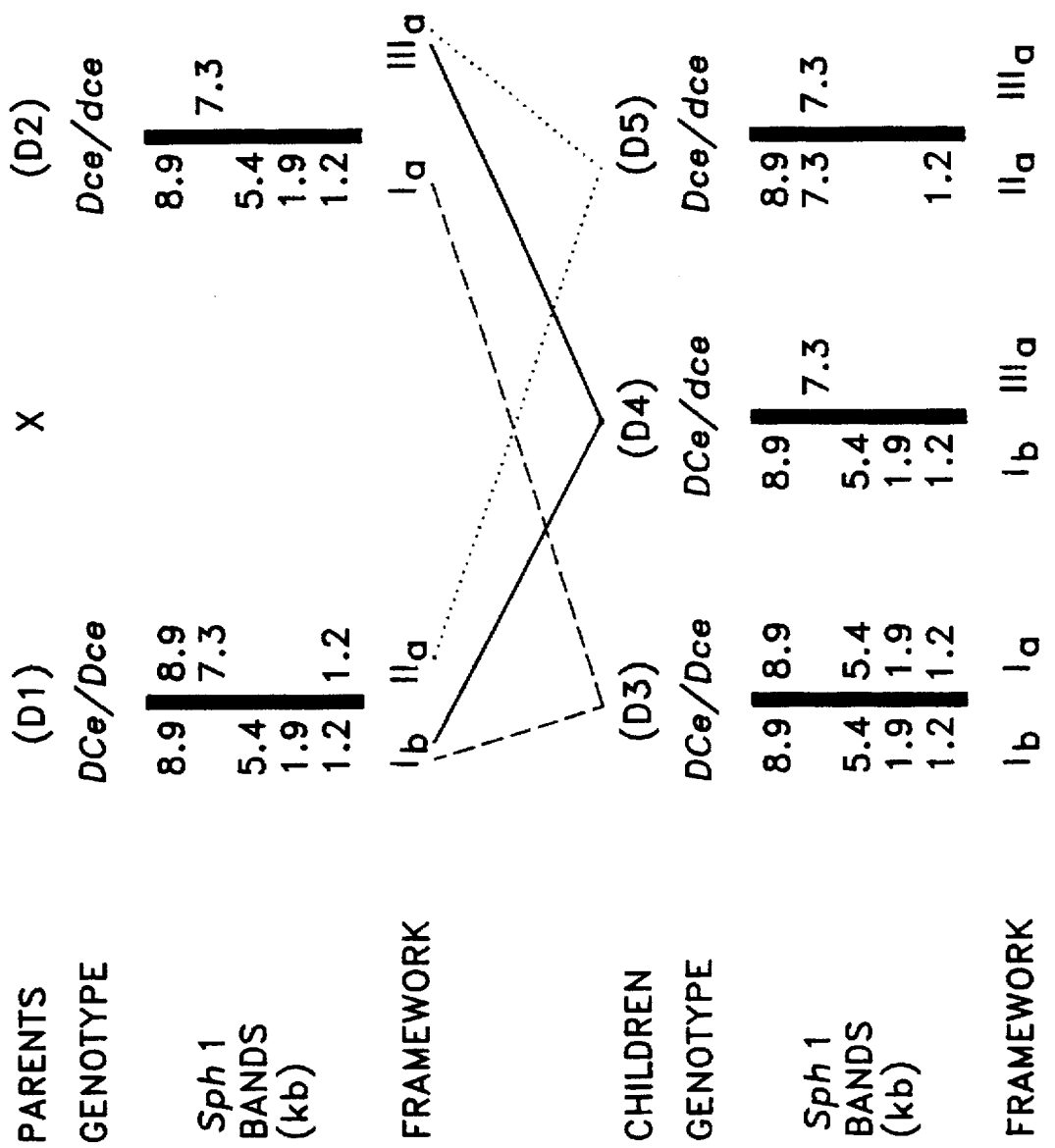
FIG. 5 is a diagram illustrating the transmission of Rh haplotypes from parents to children in a single family.

FIG. 5 shows the inheritance of Rh haplotypes in family D as deduced from the SphI banding patterns shown in FIG. 4, panel 4.Compared with D1, D2 showed reduced intensity in D gene bands. Therefore, D1 was a D/D homozygote carrying the DCe/Dce genotype, whereas D2 was a D/d heterozygote carrying the Dce/dce genotype. As the Dce haplotype in D1 and D2 was specified by different frameworks, the random assortment of parent Rh haplotypes resulted in three different genotypes in the children that matched with the SphI banding patterns (FIG. 4, panel 4) as well as the typed blood group specificities (Table 2).

EXAMPLE 4

Distribution of SphI RFLPs Among Unrelated Individuals

Figure 6:
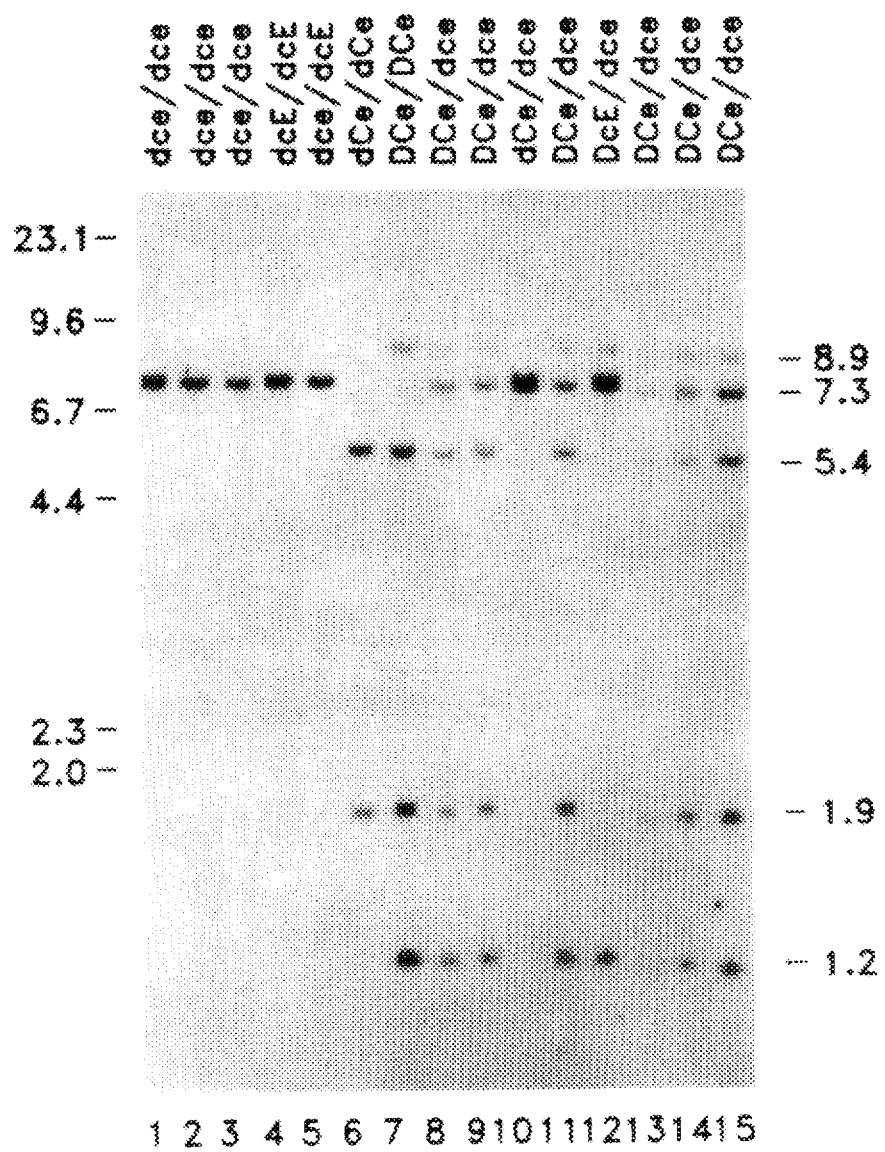
FIG. 6 shows a Southern blot of genomic DNAs from 15 unrelated random individuals prepared according to the method of the invention.

To assess whether Rh genotypes could be determined when family data are not available, we examined a number of unrelated individuals whose Rh phenotypes were serologically characterized. FIG. 6 shows a gel autoradiogram which is representative of this analysis, including seven Rh-negative and eight Rh-positive individuals. Genomic DNAs were digested with SphI, and probed with Ex4–7. Lanes 1–6 and 10 are the Rh-negative subjects, with lanes 1, 6, 10 being Caucasians, 2 being Indian, 3,5 being blacks, and 4 being Japanese. The other lanes (7–9, 11–15) are Rh-positive Caucasians, all of whom are D/d heterozygotes, except for lane 7 who is DCe/DCe homozygote. Of the total of 23 Rh-negative subjects examined, the 7.3 kb band was detectable in all except the two dCe/dCe homozygotes, and its occurrence appeared to be independent of the ethnic origin of individuals (FIG. 6). Furthermore, the D/d heterozygosity as to the DCe/dce and DcE/dce genotypes could be directly determined. This ability to directly differentiate among these genotypes was particularly significant because DCe, dce and DcE are the three most frequent haplotypes encountered in Caucasians (Ref. 6).

EXAMPLE 5

Association and Dissociation of SphI RFLPs with Rh Genetic Variants

As has been mentioned above, the Rh system is highly polymorphic, containing many low incidence antigens and variant phenotypes (Refs. 6, 39). To delineate the relationship of these low incidence antigens with SphI RFLPs, we examined 15 unrelated individuals, each carrying a distinct Rh genetic variant. This analysis revealed a complex pattern of SphI fragments indicating that the Rh phenotypic diversification has taken place on different genetic backgrounds.

Figure 7:
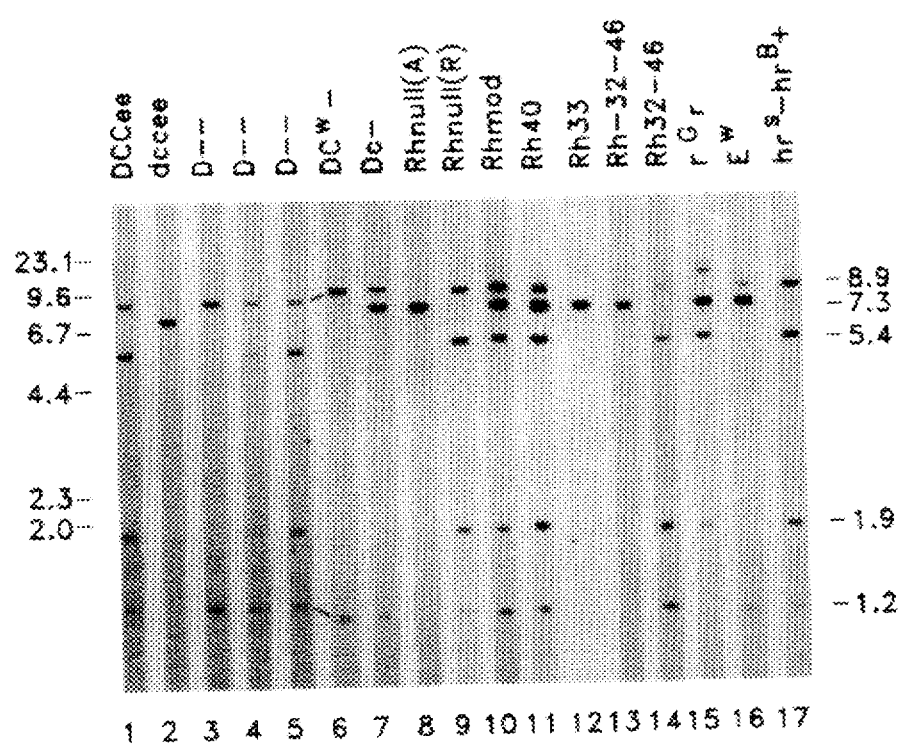
FIG. 7 shows a Southern blot of genomic DNAs from 15 unrelated individuals exhibiting variant Rh phenotypes prepared according to the method of the invention.

FIG. 7 shows Southern blots of genomic DNAs of 15 unrelated subjects exhibiting variant Rh phenotypes, which were digested with SphI and probed with Ex4–7. Lanes 1 and 2 are DCCee and dccee controls. Note that lanes 1–5 and 6–17 were run on separate agarose gels. The mobility of bands, therefore, differs between the two panels, but the correspondence of bands is indicated between lanes 5 and 6. The sizes of the various bands is noted at the right margin of the figure. Rhnull (A) and (R) denote Rhnull amorph and regulator types, respectively.

Of the five variants, the non-D antigen(s) (lanes 3–7), D– was either similar to DC$^w$–, either missing the non-D fragments or associated with a silent Ce gene. The Dc–subject apparently carried a Dce/dce genotype, yet the e antigen was not expressed. For the Rh deficiency syndromes (lanes 8–10), the amorph and regulator types of Rhnull were associated with the Rh-negative and DCe haplotypes, respectively, whereas Rhmod was accompanied by an increase of the D gene. Similar to Rhmod, Rh40 produced all five SphI bands on the genomic blot, but it was associated with an increase in Ce rather than D (lane 11). In the case of Rh33 and Rh–32, –46, both displayed the 7.3 k.b band only, suggesting their occurrence on the Rh-negative background (lanes 12 and 13). On the other hand, Rh32, –46 occurred on the DCe background with decreased intensity in the 8.9 kd band (lane 14). The r$^G$r variant lacked the D-gene fragments but contained both ce and Ce fragments (lane 15), suggesting that the marker antigen G arose from the Ce background. As to the variants of E/e series (lanes 16 and 17), the E$^W$ carrier was apparaently a DcE$^W$/dce heterozygote, most likely bearing a subtle change in the cE gene. By contrast, hr$^S$–hr$^B$+ was probably a variant of e associated with the Dce haplotype. Taken together, the results suggested that diverse molecular mechanisms have been operative in shaping the allelic diversity of Rh antigen genes (Table 3).

EXAMPLE 6

Comparison of SphI Banding Patterns between Humans and Nonhuman Primates

Figure 8:
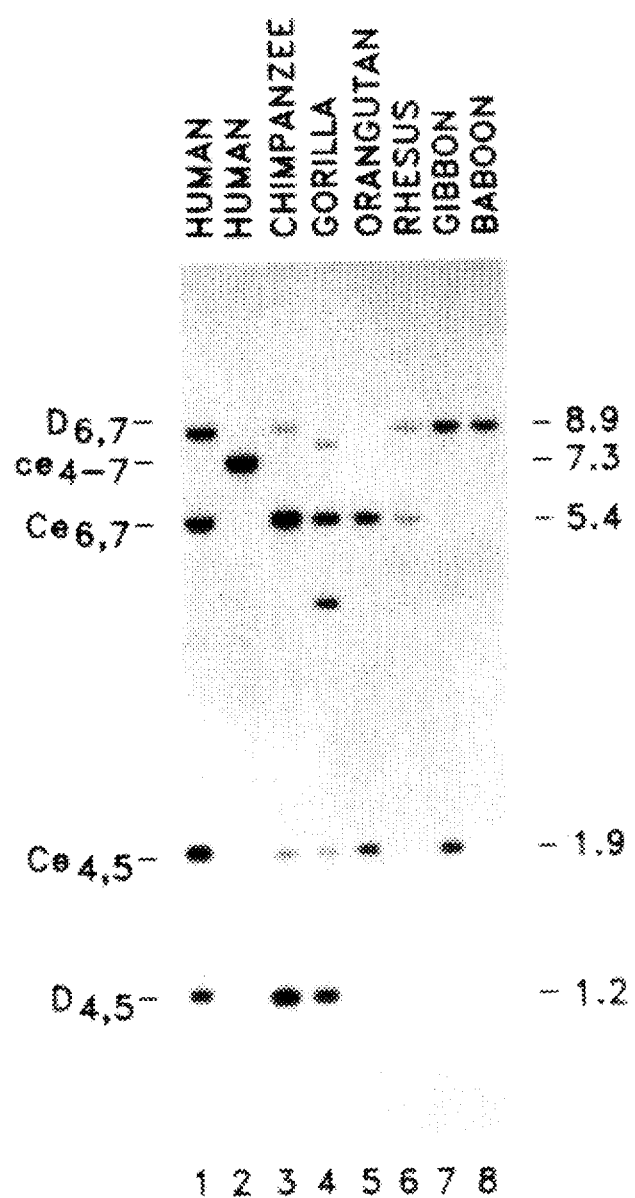
FIG. 8 shows a Southern blot of genomic DNAs from six nonhuman primates prepared according to the method of the invention.

To understand the origin of SphI frameworks in evolutionary perspective, genomic DNAs from six species of nonhuman primates were analyzed, and their SphI banding patterns were determined. As shown in FIG. 8, Rh-like genes were identified in all nonhuman primates by cross-hybridization with the human Ex4–7 probe under very stringent washing conditions, suggesting a high sequence conservation throughout primate evolution. Nevertheless, each species displayed a distinct SphI pattern, ranging from one band in baboon to five bands in gorilla. Among higher primates, the chimpanzee and gorilla appeared to be most similar to humans bearing framework I for the Dce or DCe haplotype (Table 1). This observation reconciled the expression of D- and C-analogous antigens on red cells from the two species (Ref. 40) and the presence of two or three Rh-like genes in their genomes (Ref. 41). The other four species each appeared to carry a single Rh-like gene, as they showed only one or two SphI bands corresponding to the human 1.9, 5.4 and 8.9 kb counterparts. None of the six primate species examined, however, displayed the human 7.3 kb band that defines the Rh-negative haplotypes (dce, dcE and dCE).

EXAMPLE 7

Prenatal assessment of fetuses at risk of alloimmunization

Figure 9:
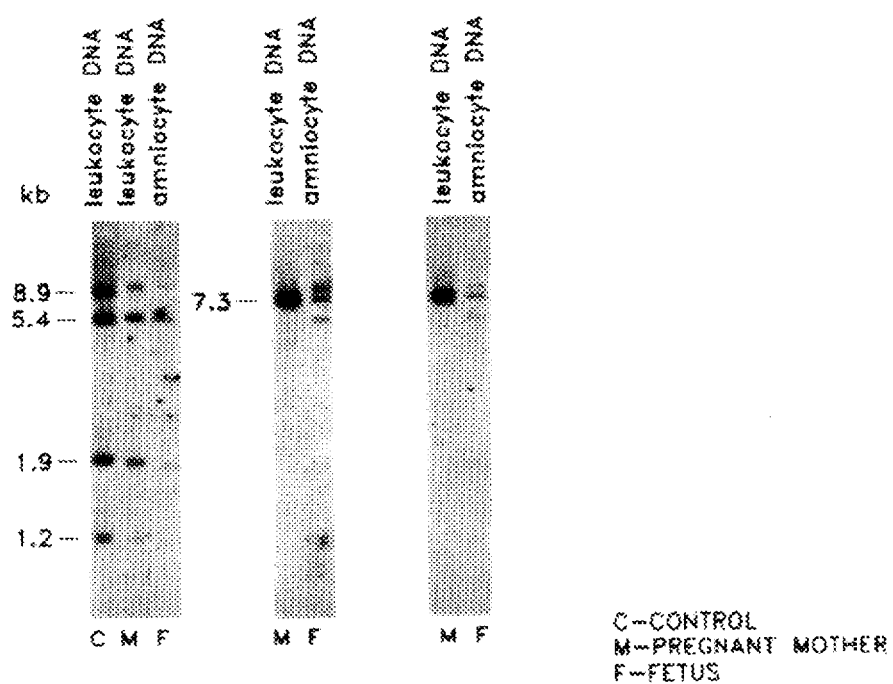
FIG. 9 shows a Southern blot of genomic DNAs from amniotic fluid of fetuses at risk of alloimmunization prepared according to the method of the invention.

To show the usefulness of SphI frameworks in prenatal assessment of fetuses at risk of Rh alloimmunization, genomic DNAs isolated from leukocytes and amniocytes (cells in amniotic fluid of pregnant women) were analyzed in parallel, and the genetic makeup of Rh genes in the fetuses were determined. FIG. 9 shows a genomic Southern blot prepared according to the method of the invention following techniques described herein. This analysis demonstrates that the D/D, D/d, or d/d status of the fetus can be unequivocally determined without prior determination on serologic typing.

In this molecular test, two mothers were found to be homozygous for dce/dce, yet they each carried a D-positive fetus heterozygous for Dce/dce (FIG. 9, middle and right panels). This finding indicated a possibility for the occurrence of letomaternal Rh alloimmunization. In the third case, both the mother and the fetus were DCe/DCe homozygotes, thus excluding the occurrence of hemolytic disease in the newborn (FIG. 9, left panel).

Without wishing to be bound by theory, we now describe the mapping and inheritance of the human Rh polypeptide genes that determine the expression of D, C, c, E, and e blood group antigens. The location of Rh at the short arm of chromosome 1 has been previously established by cytogenetic analysis (Ref. 42) and recently confirmed by in situ hybridization with the Rh cDNA probe (Refs. 43–44). The construction of the comprehensive restriction map described here, however, took advantage of the features intrinsic to the Rh genes but previously not recognized: the absence of SphI cleavage sites in their exons and the asymmetric distribution of those sites around their non-coding regions including the intronic sequences. This direct genomic mapping reveals a similar, if not identical, structural organization between the D and non-D genes and complements, respectively, the partial EcoRI map of D and the BamHI/XhoI map of CE derived from analysis of Rh genomic clones (Refs. 12, 38).

It became clear in the course of developing the invention that a set of SphI RFLPs is tightly linked with the Rh structural genes. Using exon-specific probes, we have localized the SphI polymorphic sites to the genomic region encompassing exon 4 through exon 7. Of the five SphI restriction fragments covering these four exons, the 1.2 and 8.9 kb bands were assigned to the D gene and others to the non-D genes including ce, cE, Ce and CE alleles. Analysis of informative individuals homozygous for the common Rh haplotypes revealed that these SphI fragments occur in several different banding patterns that constitute four major organizational frameworks. Family studies at the DNA level demonstrated further that such Rh frameworks are inherited en bloc in Mendelian codominant fashion, each representing a distinct combination of D (or d) with one of the alleles of the non-D gene. These results provided a molecular definition of the Rh haplotypes and established a genetic correlation of the Rh genotypes with the blood group phenotypes.

The Rh system contains nearly 50 different antigens and many variant phenotypes and, thus, is the most complex of all known red cell blood group polymorphisms (Refs. 6, 39).

The present studies on the linkage of SphI RFLPs with naturally occurring Rh variants attest to the underlying genetic heterogeneity, suggesting alterations in gene structure and/or regulatory mechanisms. As shown herein, some variants (i.e., D–, DC$^w$–, and r$^G$r) are associated with new SphI banding patterns and others occur on existing haplotype backgrounds. Although our analysis has until now been limited to just 15 variant individuals, the results indicate strongly that diversity of the Rh locus is primarily based on allelisms at the population level. This is similar to the case of other, well-characterized, human gene families, such as the major histocompatibility complex genes (Ref. 45) and the MNSs blood group system (Ref. 46).

The clinical importance of the Rh system stems from the extreme immunogenicity of its antigens and the high frequency of Rh-negative phenotypes in the population (Ref. 1). The potent antigenicity of D, C, c, E, and e epitopes remains unexplained although the hydropathy model predicts that the D and non-D Rh polypeptides are similarly organized into multiple membrane-spanning domains (Refs. 8–10). Regarding the Rh-negative haplotypes, dce occurs with a highest frequency and is most prevalent among Caucasians and Blacks (see Table 1). The extensive mapping of Rh-negative genomic DNAs shown here pinpoints d as the consequence of either a deletion or an alteration of the D gene, consistent with the results of the previous studies (Refs. 13, 47). In addition, the present studies show that the d haplotypes are specified by two different frameworks. Specifically, while dCe is associated with either the 7.3 kb or the 1.9 and 5.4 bands, dce, dcE and dCE are always associated with the 7.3 kb fragment. Whether this difference in linkage disequilibrium reflects two separate events in the evolution of Rh-negative haplotypes and whether the high incidence and ethnic confinement of dce arose from a founder effect are some questions that remain to be addressed. It is the method of the invention which now permits such detailed analysis.

Fetomaternal alloimmunization resulting from incompatible Rh blood types is still the principal cause for hemolytic disease of the newborn. Our observation that each of the four SphI frameworks is associated with a distinct Rh haplotype is immediately useful as a molecular procedure for genotyping fetuses at risk. As already demonstrated here, the SphI banding patterns in conjunction with serologic typing allow actual determination of all of the common Rh genotypes. Although changes of the SphI banding patterns have been observed (see above), they represent very rare genetic variations. Therefore, these changes should not be a major limiting factor in Rh genotype determination. Currently, the fetal D typing method depends entirely on the detection of D-specific genomic sequences by PCR amplification (Refs. 19–20), which can result in misdiagnosis for a significant number of cases (Refs. 21–23). Compared with these methods, the application of SphI frameworks to Rh genotyping will be advantageous in that: (1) the distinction of Rh zygosity related to the D/D, D/d and d/d status can be made directly and (2) the genotypes composed of non-D alleles can be deduced simultaneously. This new direct genotyping procedure will greatly facilitate genetic counseling and prenatal assessment of Rh alloimmunization.

The invention further provides diagnostic and experimental kits which include means to enable the performance of the method of the invention in a precise, accurate, and reproducible manner. The kits of the invention may include a primer or set of primers which can be used to amplify Rh DNA. The kits may include a restriction enzyme or set of restriction enzymes suitable for generating information about Rh genotype. The kits may further include positive and/or negative control reagents as well as other reagents for adapting the use of the method of the invention to particular experimental and/or diagnostic techniques as desired. The kits include one or more containers for containing the primer and/or restriction enzyme, as well as for containing any additional reagents in the kit.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

REFERENCES

1. Mollison P. L., Engelfriet C. P., and Contreras M., *Blood Transfusion in Clinical Medicine*, 9th ed., Blackwell, Oxford (1992).
2. Luban NLC, "The new and the old—Molecular diagnostics and hemolytic disease of the newborn", *New England J Med* 329(9):658–60 (1993).
3. Agre P., and Cartron J.-P., "Molecular biology of the Rh antigens", *Blood* 78:551–63 (1991).
4. Cartron J. -P., and Agre P., "Rh blood group antigens: protein and gene structure", *Semin Hematol* 30:193–208 (1993).
5. Anstee D. J., and Tanner M. J., "Biochemical aspects of the blood group Rh (rhesus) antigens", *Baillieres Clin Haematol* 6:402–22 (1993).
6. Race R. R., and Sanger R., *Blood Groups in Man*, 6th ed., Blackwell, Oxford (1975) pp. 178–260.
7. Tippett P. A., A "Speculative model for the Rh blood groups", *Ann Hum Genet* 50:241–47 (1986).
8. Chérif-Zahar B., Bloy C., Le Van Kim C., Blanchard D., Bailly P., Hermand P., Salmon C., et al., "Molecular cloning and protein structure of a human blood group Rh polypeptide", *Proc Natl Acad Sci USA* 87:6243–47 (1990).
9. Avent N. D., Ridgwell K., Tanner M. J. A., and Anstee D. J., "cDNA cloning of a 30 kDa erythrocyte membrane protein associated with Rh (Rhesus)-blood-group-antigen expression", *Biochem J* 271:821–25 (1990).
10. Le Van Kim C., Mouro I., Chérif-Zahar B., Raynal V., Cherrier C., Cartron J.-P., and Colin Y., "Molecular cloning and primary structure of the human blood group RhD polypeptide", *Proc Natl Acad Sci USA* 89:10925–29 (1992).
11. Kajii E., Umenishi F., Iwamoto S., and Ikemoto S., "Isolation of a new cDNA clone encoding an Rh polypeptide associated with the Rh blood group system", *Hum Genet* 91:157–62 (1993).
12. Arce M. A., Thompson E. S., Wagner S., Coyne K. E., Ferdman B. A., and Lublin D. M., "Molecular cloning of RhD cDNA derived from a gene present in RhD-positive, but not RhD-negative individuals", *Blood* 82:651–55 (1993).
13. Colin Y., Chérif-Zahar B., Le Van Kim C., Raynal V., Van Huffel V., and Cartron J. -P., "Genetic basis of the RhD-positive and RhD-negative blood group polymorphism as determined by Southern analysis", *Blood* 78:2747–52 (1991).
14. Mouro I., Colin Y., Chérif-Zahar B., Cartron J.- P., and Le Van Kim C., "Molecular genetic basis of the human Rhesus blood group system", *Nature Genet* 5:62–65 (1993).
15. Walker R. H. et al., eds., *Technical Manual*, 11th ed., American Association of Blood Banks, Arlington, Va. (1993)
16. Zelinski T., "The use of DNA restriction fragment length polymorphisms in conjunction with blood group serology", *Transfusion*, 31:762–70 (1991).
17. Hopkinson D. A., "The long [E/e] and the short [C/c] of the rhesus polymorphism", *Nature Genetics* 5:6–7 (1993).

18. Le Van Kim C., Chérif-Zahar B., Rayhal V., Mouro I., Lopez M., Cartron J. -P., and Colin Y., "Multiple Rh messenger RNA isoforms are produced by alternative splicing", *Blood* 80:1074–78 (1992).
19. Bennett P. R., Le Van Kim C., Colin Y., Warwick R. M., Chérif-Zahar B., Fisk N. M., and Cartron J. -P., "Prenatal determination of fetal RhD type of DNA amplification", *New England J Med* 329:607–10 (1993).
20. Fisk N. M., Bennett P., Warwick R. M., Letsky E. A., Welch R., Vaughn J. I., and Moore G., "Clinical utility of fetal RhD typing in alloimmunized pregnancies by means of polymerase chain reaction on amniocytes or chorionic villi", *Am J Obstet Gynecol* 171:50–54 (1994).
21. Carritt B., Steers F. J., and Avent N. D., "Prenatal determination of fetal RhD type", *Lancet* 344:205–06 (1994) (Letter).
22. Simsek S., Bleeker P. M., and von dem Borne A. E., "Prenatal determination of fetal RhD type", *New England J Med* 339:795–96 (1994).
23. Bennett P., Warwick R., and Cartron J. -P., *New England J Med* 330(11):795–96 (1994) (Response to letter by Simsek et al.).
24. Sambrook J., Fritsch E. F., and Maniatis T., *Molecular Cloning: A Laboratory Manual*, 2d. ed., Cold Spring Harbor Laboratory, New York (1989).
25. Innis M. A., Gelfand D. H., Sninsky J. J., and White T. J., *PCR Protocols: A Guide to Methods and Applications*, Academic Press, Inc., San Diego (1990).
26. Landegren U., et al., *Science* 241:1077 (1988).
27. Barany F., *PCR Methods and Applications* 1:5 (1991).
28. Narang et al., *Methods Enzymol* 68:90 (1979).
29. Brown et al., *Methods Enzymol* 68:109 (1979).
30. Beaucage et al., *Tetrahedron Lett* 22:1859 (1981).
31. Huang C.-H., Guizzo M. L., McCreary J., Leigh E. M., and Blumenfeld O. O., "Typing of MNSs blood group specific sequences in the human genome and characterization of a restriction fragment tightly linked to S-s- alleles", *Blood* 77:381–86 (1991).
32. Goossens M., and Kan Y. Y., "DNA analysis in the diagnosis of hemoglobin disorders", *Methods Enzymol* 76:805–17 (1981).
33. Huang C.-H., Reid M. E., and Chen Y., "Identification of a partial internal deletion in the RH locus causing the erythrocyte D–phenotype", *Blood* (In Press).
34. Saiki R. K., Gelfand D. H., Stoffel S., Scharf S. J., Higuchi R., Horns G. T., Mullis K. B., et al., "Primer-directed enzymatic amplification of DNA with a thermostable DNA polymerase", *Science* 239:487–91 (1988).
35. Southern E. M., "Gel electrophoresis of restriction fragments", *Methods Enzymol* 68:152–76 (1979).
36. Huang C. -H., and Blumenfeld O. O., "Characterization of a genomic hybrid specifying the human erythrocyte antigen Dantu: Dantu gene is duplicated and linked to a delta glycophorin gene deletion", *Proc Natl Acad Sci USA* 85:9640–44 (1988).
37. Feinberg A. P., and Vogelstein B., "A technique for radiolabeling DNA restriction endonuclease fragments to high specific activity" *Anal Biochem* 137:266–67 (1984).
38. Chérif-Zahar B., Le Van Kim C., Rouillac C., Rayhal V., Cartron J. -P., and Colin Y., "Organization of the gene (RHCE) encoding the human blood group RhCcEe antigens and characterization of the promoter region", *Genomics* 19:68–74 (1994).
39. Issitt P. D., "The Rh blood group system (1988: Eight new antigens in nine years and some observations on the biochemistry and genetics of the system", *Transfusion Med Rev* 3:1–12 (1989).
40. Socha W. W., and Ruffie J., *Blood Groups of Primates: Theory, Practice and Evolutionary Meaning*, pp. 75–90, Alan Liss, New York (1983).
41. Salvignol L., Blancher A., Calvas P., Socha W. W., Colin Y., Cartron J. -P., and Ruffie J., "Relationship between chimpanzee Rh-like genes and the R-C-E-F blood group system", *J Med Primatol* 22:19–28 (1993).
42. Marsh W. L., Chaganti R. S., Gardner F. H., Mayer K., Nowell P. C., and German J., "Mapping human autosomes: evidence supporting assignment of rhesus to the short arm of chromosome No. 1", *Science* 183:966–68 (1974).
43. Chérif-Zahar B., Mattei M. G., Le Van Kim C., Bailly P., Carton J. -P., and Colin Y., "Localization of the human Rh blood group gene structure to chromosome region 1 p34.3-1 p36.1 by in situ hybridization", *Hum Genet* 86:398–400 (1991).
44. MacGeoch C., Mitchell C. J., Carritt B., Avent N. D., Ridgwell K., Tanner M. J., and Spurr N. K., "Assignment of the chromosomal locus of the human 30-kDal Rh (rhesus) blood group-antigen-related protein (Rh30 A) to chromosome region 1 p36.13–p34" *Cytogenet Cell Genet* 59:261–63 (1992).
45. Kappes D., and Strominger J. L., "Human class II major histocompatibility complex genes and proteins", *Ann Rev Biochem* 57:991–1028 (1988).
46. Huang C. -H., and Blumenfeld O. O., "MNSs blood groups and major glycophorins: Molecular basis for allelic variation", in Cartron J. -P., and Rouger P., (eds.), *Blood Cell Biochemistry* 6:153–88, Plenum Press, New York (1995).
47. Hyland C. A., Wolter L. C., and Saul A., "Three unrelated Rh D gene polymorphisms identified among blood donors with Rhesus CCee (r'r') phenotypes", *Blood* 84:321–24 (1994).

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 1384 nucleotides
( B ) TYPE: nucleic acid
( C ) STRANDEDNESS: double
( D ) TOPOLOGY: linear ( x i ) SEQUENCE DESCRIPTION: SEQ ID NO:1:

-continued

```
AATCCCGGCC TGCACAGAGA CGGACACAGG
                              ATG AGC TCT AAG TAC CCG CGG TCT GTC CGG      60
CGC TGC CTG CCC CTC TGG GCC CTA ACA CTG GAA GCA GCT CTC ATT             105
CTC CTC TTC TAT TTT TTT ACC CAC TAT GAC GCT TCC TTA GAG GAT             150
CAA AAG GGG CTC GTG GCA TCC TAT CAA GTC GGC CAA GAT CTG ACC             195
GTG ATG GCG GCC CTT GGC TTG GGC TTC CTC ACC TCA AAT TTC GGG             240
AGA CAC AGC TGG AGC AGT GTG GCC TTC AAC CTC TTC ATG CTG GCG             285
CTT GGT GTG CAG TGG GCA ATC CTG CTG GAC GGC TTC CTG AGC CAG             330
TTC CCT CCT GGG AAG GTG GTC ATC ACA CTG TTC AGT ATT CGG CTG             375
GCC ACC ATG AGT GCT ATG TCG GTG CTG ATC TCA GCG GGT GCT GTC             420
TTG GGG AAG GTC AAC TTG GCG CAG TTG GTG GTG ATG GTG CTG GTG             465
GAG GTG ACA GCT TTA GGC ACC CTG AGG ATG GTC ATC AGT AAT ATC             510
TTC AAC ACA GAC TAC CAC ATG AAC CTG AGG CAC TTC TAC GTG TTC             555
GCA GCC TAT TTT GGG CTG ACT GTG GCC TGG TGC CTG CCA AAG CCT             600
CTA CCC AAG GGA ACG GAG GAT AAT GAT CAG AGA GCA ACG ATA CCC             645
AGT TTG TCT GCC ATG CTG GGC GCC CTC TTC TTG TGG ATG TTC TGG             690
CCA AGT GTC AAC TCT CCT CTG CTG AGA AGT CCA ATC AAA GGG AAG             735
AAT GCC ATG TTC AAC ACC TAC TAT GCT CTA GCA GTC AGT GTG GTG             780
ACA GCC ATC TCA GGG TCA TCC TTG GCT CAC CCC CAA AGG AAG ATC             825
AGC ATG ACT TAT GTG CAC AGT GCG GTG TTG CAG GAG GC GTG GCT              870
GTG GGT ACC TCG TGT CAC CTG ATC CCT TCT CCG TGG CTT GCC ATG             915
GTG CTG GGT CTT GTG GCT GGG CTG ATC TCC ATC GGG GGA GCC AAG             960
TGC CTG CCG GTG TGT TGT AAC CGA GTG CTG GGG ATT CAC CAC ATC            1005
TCC GTC ATG CAC TCC ATC TTC AGC TTG CTG GGT CTG CTT GGA GAG            1050
ATC ACC TAC ATT GTG CTG CTG GTG CTT CAT ACT GTC TGG AAC GGC            1095
AAT GGC ATG ATT GGC TTC CAG GTC CTC CTC AGC ATT GGG AAC TC             1140
AGC TTG GCC ATC GTG ATA GCT CTC ACG TCT GGT CTC CTG ACA GGT            1185
TTG CTC CTA AAT CTC AAA ATA TGG AAA GCA CCT CAT GTG GCT AAA            1230
TAT TTT GAT GAC CAA GTT TTC TGG AAG TTT CCT CAT TTG GCT GTT            1275
GGA TTT TAAGCAAAAG CATCCAAGAA AAACAAGGCC TGTTCAAAAA CAAGACAACT         1331
TCCTCTCACT GTTGCCTGCA TTTGTACGTG AGAAACGCTC ATGACAGCAA AGT             1384
```

( 2 ) INFORMATION FOR SEQ ID NO:2:

( i ) SEQUENCE CHARACTERISTICS:
        ( A ) LENGTH: 1466 nucleotides
        ( B ) TYPE: nucleic acid
        ( C ) STRANDEDNESS: double
        ( D ) TOPOLOGY: linear ( x i ) SEQUENCE DESCRIPTION: SEQ ID NO:2:

```
GATGCCTGGT GCTGGTGGAA CCCCTGCACA GAGACGGACA CAGG ATG AGC TCT AAG TAC    59
CCG CGG TCT GTC CGG CGC TGC CTG CCC CTC TGG GCC CTA ACA CTG            104
GAA GCA GCT CTC ATT CTC CTC TTC TAT TTT TTT ACC CAC TAT GAC            149
```

-continued

```
GCT TCC TTA GAG GAT CAA AAG GGG CTC GTG GCA TCC TAT CAA GTC        194

GGC CAA GAT CTG ACC GTG ATG GCG GCC CTT GGC TTG GGC TTC CTC        239

ACC TCA AAT TTC CGG AGA CAC AGC TGG AGC AGT GTG GCC TTC AAC        284

CTC TTC ATG CTG GCG CTT GGT GTG CAG TGG GCA ATC CTG CTG GAC        329

GGC TTC CTG AGC CAG TTC CCT CCT GGG AAG GTG GTC ATC ACA CTG        374

TTC AGT ATT CGG CTG GCC ACC ATG AGT GCT ATG TCG GTG CTG ATC        419

TCA GCG GGT GCT GTC TTG GGG AAG GTC AAC TTG GCG CAG TTG GTG        464

GTG ATG GTG CTG GTG GAG GTG ACA GCT TTA GGC ACC CTG AGG ATG        509

GTC ATC AGT AAT ATC TTC AAC ACA GAC TAC CAC ATG AAC CTG AGG        554

CAC TTC TAC GTG TTC GCA GCC TAT TTT GGG CTG ACT GTG GCC TGG        599

TGC CTG CCA AAG CCT CTA CCC AAG GGA ACG GAG GAT AAT GAT CAG        644

AGA GCA ACG ATA CCC AGT TTG TCT GCC ATG CTG GGC GCC CTC TTC        689

TTG TGG ATG TTC TGG CCA AGT GTC AAC TCT CCT CTG CTG AGA AGT        734

CCA ATC CAA AGG AAG AAT GCC ATG TTC AAC ACC TAC TAT GCT CTA        779

GCA GTC AGT GTG GTG ACA GCC ATC TCA GGG TCA TCC TTG GCT CAC        824

CCC CAA AGG AAG ATC AGC ATG ACT TAT GTG CAC AGT GCG GTG TTG        869

GCA GGA GGC GTC GCT GTG GGT ACC TCG TGT CAC CTG ATC CCT TCT        914

CCG TGG CTT GCC ATG GTG CTG GGT CTT GTG GCT GGG CTG ATC TCC        959

ATC GGG GGA GCC AAG TGC CTG CCG GTG TGT TGT AAC CGA GTG CTG       1004

GGG ATT CAC CAC ATC TCC GTG ATG CAC TCC ATC TTC AGC TTG CTG       1049

GGT CTG CTT GGA GAG ATC ACC TAC ATT GTG CTG CTG GTG CTT CAT       1094

ACT GTC TGG AAC GGC AAT GGC ATG ATT GGC TTC CAG GTC CTC CTC       1139

AGC ATT GGG GAA CTC AGC TTG GCC ATC GTG ATA GCT CTC ACG TCT       1184

GGT CTC CTG ACA GGT TTG CTC CTA AAT CTC AAA ATA TGG AAA GCA       1229

CCT CAT GTG GCT AAA TAT TTT GAT GAC CAA GTT TTC TGG AAG TTT       1274

CCT CAT TTG GCT GTT GGA TTT TAAGCAAAAG CATCCAAGAA AAACAAGGCC      1325

TGTTCAAAAA CAAGACAACT TCCTCTCACT GTTGCCTGCA TTTGTACGTG AGAAACGCTC 1385

ATGACAGCAA AGTCTCCTTA TGTATAATGA AACAAGGTCA GAGACAGATT TGATATTAAA 1445

AAATTAAAAA AAAAAAAAAA A                                           1466
```

( 2 ) INFORMATION FOR SEQ ID NO:3:

( i ) SEQUENCE CHARACTERISTICS:
        ( A ) LENGTH: 417 amino acids
        ( B ) TYPE: amino acid
        ( C ) TOPOLOGY: linear ( i i ) MOLECULE TYPE: peptide ( i i i ) SEQUENCE DESCRIPTION: SEQ ID NO:3:

```
Met Ser Ser Lys Tyr Pro Arg Ser Val Arg Arg Cys Leu Pro Leu
 1               5                  10                  15

Trp Ala Leu Thr Leu Glu Ala Ala Leu Ile Leu Leu Phe Tyr Phe
                20                  25                  30

Phe Thr His Tyr Asp Ala Ser Leu Glu Asp Gln Lys Gly Leu Val
                35                  40                  45

Ala Ser Tyr Gln Val Gly Gln Asp Leu Thr Val Met Ala Ala Leu
```

|     |     |     |     | 50  |     |     |     |     | 55  |     |     |     |     | 60  |
|-----|-----|-----|-----|-----|-----|-----|-----|-----|-----|-----|-----|-----|-----|-----|
| Gly | Leu | Gly | Phe | Leu<br>65 | Thr | Ser | Asn | Phe | Arg<br>70 | Arg | His | Ser | Trp | Ser<br>75 |
| Ser | Val | Ala | Phe | Asn<br>80 | Leu | Phe | Met | Leu | Ala<br>85 | Leu | Gly | Val | Gln | Trp<br>90 |
| Ala | Ile | Leu | Leu | Asp<br>95 | Gly | Phe | Leu | Ser | Gln<br>100 | Phe | Pro | Pro | Gly | Lys<br>105 |
| Val | Val | Ile | Thr | Leu<br>110 | Phe | Ser | Ile | Arg | Leu<br>115 | Ala | Thr | Met | Ser | Ala<br>120 |
| Met | Ser | Val | Leu | Ile<br>125 | Ser | Ala | Gly | Ala | Val<br>130 | Leu | Gly | Lys | Val | Asn<br>135 |
| Leu | Ala | Gln | Leu | Val<br>140 | Val | Met | Val | Leu | Val<br>145 | Glu | Val | Thr | Ala | Leu<br>150 |
| Gly | Thr | Leu | Arg | Met<br>155 | Val | Ile | Ser | Asn | Ile<br>160 | Phe | Asn | Thr | Asp | Tyr<br>165 |
| His | Met | Asn | Leu | Arg<br>170 | His | Phe | Tyr | Val | Phe<br>175 | Ala | Ala | Tyr | Phe | Gly<br>180 |
| Leu | Thr | Val | Ala | Trp<br>185 | Cys | Leu | Pro | Lys | Pro<br>190 | Leu | Pro | Lys | Gly | Thr<br>195 |
| Glu | Asp | Asn | Asp | Gln<br>200 | Arg | Ala | Thr | Ile | Pro<br>205 | Ser | Leu | Ser | Ala | Met<br>210 |
| Leu | Gly | Ala | Leu | Phe<br>215 | Leu | Trp | Met | Phe | Trp<br>220 | Pro | Ser | Val | Asn | Ser<br>225 |
| Pro | Leu | Leu | Arg | Ser<br>230 | Pro | Ile | Gln | Arg | Lys<br>235 | Asn | Ala | Met | Phe | Asn<br>240 |
| Thr | Tyr | Tyr | Ala | Leu<br>245 | Ala | Val | Ser | Val | Val<br>250 | Thr | Ala | Ile | Ser | Gly<br>255 |
| Ser | Ser | Leu | Ala | His<br>260 | Pro | Gln | Arg | Lys | Ile<br>265 | Ser | Met | Thr | Tyr | Val<br>270 |
| His | Ser | Ala | Val | Leu<br>275 | Ala | Gly | Gly | Val | Ala<br>280 | Val | Gly | Thr | Ser | Cys<br>285 |
| His | Leu | Ile | Pro | Ser<br>290 | Pro | Trp | Leu | Ala | Met<br>295 | Val | Leu | Gly | Leu | Val<br>300 |
| Ala | Gly | Leu | Ile | Ser<br>305 | Ile | Gly | Gly | Ala | Lys<br>310 | Cys | Leu | Pro | Val | Cys<br>315 |
| Cys | Asn | Arg | Val | Leu<br>320 | Gly | Ile | His | His | Ile<br>325 | Ser | Val | Met | His | Ser<br>330 |
| Ile | Phe | Ser | Leu | Leu<br>335 | Gly | Leu | Leu | Gly | Glu<br>340 | Ile | Thr | Tyr | Ile | Val<br>345 |
| Leu | Leu | Val | Leu | His<br>350 | Thr | Val | Trp | Asn | Gly<br>355 | Asn | Gly | Met | Ile | Gly<br>360 |
| Phe | Gln | Val | Leu | Leu<br>365 | Ser | Ile | Gly | Glu | Leu<br>370 | Ser | Leu | Ala | Ile | Val<br>375 |
| Ile | Ala | Leu | Thr | Ser<br>380 | Gly | Leu | Leu | Thr | Gly<br>385 | Leu | Leu | Leu | Asn | Leu<br>390 |
| Lys | Ile | Trp | Lys | Ala<br>395 | Pro | His | Val | Ala | Lys<br>400 | Tyr | Phe | Asp | Asp | Gln<br>405 |
| Val | Phe | Trp | Lys | Phe<br>410 | Pro | His | Leu | Ala | Val<br>415 | Gly | Phe |     |     |     |

What is claimed is:

1. A diagnostic method for determining Rh genotype of a subject, comprising:

isolating a DNA sample from a subject;

selectively cleaving the isolated DNA sample by digesting the DNA sample with SphI restriction enzyme to provide Rh gene fragments which are differentially characteristic of an Rh zygosity; and detecting and correlating the Rh gene fragments so to determine Rh zygosity of the subject.

2. The diagnostic method of claim 1, wherein said Rh gene fragments are differentially characteristic of RhDd zygosity.

3. The diagnostic method of claim 1, wherein said Rh gene fragments are differentially characteristic of RhCc zygosity.

4. The diagnostic method of claim 1, wherein said Rh gene fragments are differentially characteristic of RhEe zygosity.

5. The diagnostic method of claim 1, wherein said Rh gene fragments are differentially characteristic of RhCcEe zygosity.

6. The diagnostic method of claim 1, wherein said Rh gene fragments are differentially characteristic of RhDd and RhCcEe zygosity.

7. The diagnostic method according to claim 1, further comprising selectively amplifying said DNA sample.

8. The diagnostic method of claim 7, wherein said selectively amplifying step includes amplifying said DNA sample by polymerase chain reaction, ligase chain reaction, or a combination thereof.

9. The diagnostic method of claim 7, wherein said selectively amplifying step comprises amplifying said DNA sample by at least one primer which amplifies RhD DNA.

10. The diagnostic method of claim 7, wherein said selectively amplifying step comprises amplifying said DNA sample by at least one primer which amplifies RhCcEe DNA.

11. The diagnostic method of claim 7, wherein said selectively amplifying step comprises amplifying said DNA sample by at least one primer which amplifies RhD DNA and at least one primer which amplifies RhCcEe DNA.

12. The diagnostic method of claim 7, wherein said selectively amplifying step comprises amplifying said DNA sample by a primer which amplifies RhD DNA and RhCcEe DNA.

13. The diagnostic method of claim 1, wherein said detecting step further comprises:

separating said Rh DNA fragments according to size to obtain a Rh fragment pattern, wherein said Rh fragment pattern provides information specifically characterizing the Rh zygosity of the subject.

14. The diagnostic method of claim 13, wherein said detecting step includes marking one or more of said Rh DNA fragments with a hybridization probe composition.

15. The diagnostic method of claim 13, wherein said detecting step includes marking one or more of said Rh DNA fragments with a hybridization probe composition that binds to RhD and RhCcEe DNA.

16. The diagnostic method of claim 15, wherein said marking step includes marking one or more of said Rh DNA fragments with a hybridization probe composition comprising a hybridization probe specific for an RhD DNA fragment.

17. The diagnostic method of claim 15, wherein said marking step includes marking one or more of said Rh DNA fragments with a hybridization probe composition comprising a hybridization probe specific for an RhCcEe DNA fragment.

18. The diagnostic method of claim 1, further comprising determining a non-Rh genotype of said subject.

19. The diagnostic method of claim 1, further comprising determining an Rh phenotype of said subject.

20. The diagnostic method of claim 26, wherein said determining step comprises determining an Rh phenotype of said subject by serological testing.

21. The diagnostic method of claim 1, wherein said DNA sample is isolated from erythroid tissue of the subject.

22. The diagnostic method of claim 21, wherein said DNA sample is isolated from amniotic fluid or chorionic villas and wherein said subject is a fetus.

23. The diagnostic method of claim 21, wherein said erythroid tissue is a blood sample.

24. The diagnostic kit for the determination of Rh genotype, comprising:

(a) a first reagent container including at least one primer which specifically amplifies Rh DNA; and (b) a second reagent container including SphI restriction enzyme which cleaves Rh DNA to provide Rh DNA fragments characterizing an Rh zygosity.

25. The diagnostic kit of claim 24, wherein said at least one primer comprises a primer which amplifies RhD DNA and RhCcEe DNA.

26. The diagnostic kit of claim 24, wherein said at least one primer comprises a primer which amplifies Rh DNA selected from the group consisting of RhD DNA, RhCc DNA, RhEa DNA, RhCcEe DNA, RhDCcEe DNA, and combinations thereof.

27. The diagnostic kit of claim 24, wherein said kit further comprises means for separating Rh DNA fragments.

28. The diagnostic kit of claim 27, wherein said separating means comprises means for separating Rh DNA fragments on the basis of molecular weight, electrophoretic mobility, or chromatographic mobility.

29. The diagnostic kit of claim 24, wherein said kit further comprises means for detecting Rh DNA.

30. The diagnostic kit of claim 24, wherein said kit further comprises means for detecting Rh phenotype.

31. The diagnostic kit of claim 30, wherein said Rh phenotype detecting means comprises means for determining Rh phenotype serologically.

32. The diagnostic kit of claim 24, wherein said kit further comprises means for acquiring a biological sample from a subject.

33. A diagnostic kit according to claim 24, wherein said kit further comprises:

(c) a third reagent container including a hybridization probe composition for marking one or more of said Rh DNA fragments.

34. A diagnostic kit according to claim 33, wherein said hybridization probe composition comprises a hybridization probe that specifically binds to an RhD DNA fragment.

35. A diagnostic kit according to claim 33, wherein said hybridization probe composition comprises a hybridization probe that specifically binds to an RhCcEe DNA fragment.

36. A diagnostic kit for the determination of Rh genotype, comprising:

(a) a first reagent including SphI restriction enzyme which cleaves Rh DNA to provide Rh DNA fragments characterizing an Rh zygosity; and (b) a second reagent container including a hybridization probe composition for marking one or more of said Rh DNA fragments.

37. A diagnostic kit according to claim 36, wherein said hybridization probe composition comprises a hybridization probe that specifically binds to an RhD DNA fragment.

38. A diagnostic kit according to claim 36, wherein said hybridization probe composition comprises a hybridization probe that specifically binds to an RhCcEe DNA fragment.

39. A diagnostic kit according to claim 36, wherein said hybridization probe composition comprises a hybridization probe that specifically binds to RhD and RhCcEe DNA.

* * * * *